(12) United States Patent
Li et al.

(10) Patent No.: US 7,649,013 B2
(45) Date of Patent: Jan. 19, 2010

(54) METHODS OF PROTECTING AGAINST RADIATION INJURY

(75) Inventors: Chiang J. Li, West Roxbury, MA (US); Stephen A. Hill, Boxford, MA (US); YouZhi Li, Westwood, MA (US)

(73) Assignee: ArQule, Inc., Woburn, MA (US)

( * ) Notice: Subject to any disclaimer, the term of this patent is extended or adjusted under 35 U.S.C. 154(b) by 632 days.

(21) Appl. No.: 10/995,565

(22) Filed: Nov. 24, 2004

(65) Prior Publication Data

US 2006/0223880 A1    Oct. 5, 2006

Related U.S. Application Data

(60) Provisional application No. 60/570,096, filed on May 12, 2004, provisional application No. 60/561,901, filed on Apr. 14, 2004, provisional application No. 60/525,341, filed on Nov. 26, 2003.

(51) Int. Cl.
*A61K 31/355* (2006.01)
*A61K 31/12* (2006.01)
*A61K 31/35* (2006.01)

(52) U.S. Cl. ............... 514/455; 514/680; 514/454

(58) Field of Classification Search ............... None
See application file for complete search history.

(56) References Cited

U.S. PATENT DOCUMENTS

| | | | |
|---|---|---|---|
| 3,920,808 A | 11/1975 | Fusaro | |
| 5,424,073 A | 6/1995 | Rahman et al. | 424/450 |
| 5,624,908 A * | 4/1997 | Bicher | 514/23 |
| 5,728,680 A * | 3/1998 | Morozov et al. | 514/19 |
| 5,763,625 A * | 6/1998 | Boothman et al. | 549/390 |
| 5,824,700 A | 10/1998 | Frydman et al. | |
| 5,869,338 A | 2/1999 | Grdina | |
| 5,969,163 A | 10/1999 | Frydman et al. | |
| 6,054,467 A * | 4/2000 | Gjerset | 514/309 |
| 6,245,807 B1 | 6/2001 | Pardee et al. | |
| 6,498,192 B1 * | 12/2002 | Johnson et al. | 514/564 |
| 6,667,346 B2 | 12/2003 | Reddy et al. | |
| 6,706,927 B2 | 3/2004 | Reddy et al. | |
| 6,809,176 B2 * | 10/2004 | Blokhin et al. | 530/300 |
| 7,279,290 B2 * | 10/2007 | Kastan et al. | 435/7.1 |
| 7,368,440 B2 * | 5/2008 | Cassatt et al. | 514/114 |
| 2003/0091639 A1 * | 5/2003 | Jiang et al. | 424/486 |
| 2005/0170368 A1 * | 8/2005 | Ashkenazi et al. | 435/6 |
| 2005/0272120 A1 * | 12/2005 | Dowd et al. | 435/69.1 |
| 2006/0015952 A1 * | 1/2006 | Filvaroff | 800/10 |
| 2006/0247306 A1 * | 11/2006 | Kumar et al. | 514/458 |

FOREIGN PATENT DOCUMENTS

| | | |
|---|---|---|
| WO | WO 94/04145 A1 | 3/1994 |
| WO | WO 95/07700 A1 | 3/1995 |
| WO | WO 00/61142 A1 | 10/2000 |
| WO | WO 03/090710 A1 | 11/2003 |
| WO | WO 2004/007531 A2 | 1/2004 |
| WO | WO 2004/007531 A3 | 1/2004 |
| WO | WO 2004/045557 A2 | 6/2004 |
| WO | WO 2004/045557 A3 | 6/2004 |

OTHER PUBLICATIONS

Pink et al. NAD(P)H:quinone oxidoreductase activity is the principal determinant of β-lapachone cytotoxicity. J Biol Chem. Feb. 25, 2000;275(Issue 8): 5416-5424, electronic copy, pp. 1-19.*

Boothman et al. Potentiation of halogentated pyrimidine radiosensitizers in human carcinoma cells by β-lapachone (3,4-dihydro-2,2-dimethyl-2H-naphthol-[1,2-b]-pyran-5,6-dione), a novel DNA repair inhibitor. Cancer Research. 1987;47:5361-5366.*

Wuerzberger et al. Induction of apoptosis in MCF-7:WS8 breast cancer cells by β-Lapachone. Cancer Research. May 1, 1998; 58: 1876-1885.*

Websters New Collegiate Dictionary. 1981, p. 905.*

(Scolaro et al. Electron-Beam therapy for AIDS-related molluscum contagiosum lesions: preliminary experience. Radiology. 1999; 210:479-482.*

Bootman et al. Inhibition of radiation-induced neoplastic transformation by β-lapachone. Proc. Natl. Acad. Sci. 1989;86:4963-4867.*

Goncalves et al., "Evaluation of the Toxicity of 3-Allyl-β-Lapachone Against Trypanosoma Cruzi Bloodstream Forms", *Mol. Biochem. Parasitology*, 1:167-176 (1980).

Goncalves et al., "Substancias antimicrobianas de plantas superiors", *Revista Do Instituto De Antibioticos*, 4(1/2):3-17 (1962) (Discussion in English).

Hooker, S.C., "Lomatiol. Part II. Its Occurrence, Constitution, Relation to and Conversion into Lapachol. Also a Synthesis of Lapachol.", J. Am. Chem. Soc., 58(7):1181-1190 (1936).

Li et al., "Three inhibitors of type 1 human immunodeficiency virus long terminal repeatdirected gene expression and virus replication", *Proc. Nat'l. Acad. Sci. U.S.A.*, 90:1839-1842 (1993).

Schaffner-Sabba et al., "β-Lapachone: Synthesis of Derivatives and Activities in Tumor Models",*J. Med. Chem.*, 27:990-994 (1984).

Schuerch et al., "β-Lapachone, an Inhibitor of Oncornavirus Reverse Transcriptase and Eukaryotic DNA Polymerase-α", *Eur. J. Biochem.*, 84:197-205 (1978).

International Search report mailed in PCT/US2004/039647 on Jun. 15, 2005.

(Continued)

*Primary Examiner*—Charlesworth Rae
(74) *Attorney, Agent, or Firm*—Mintz, Levin, Cohn, Ferris, Glovsky and Popeo, PC; Ivor R. Elrifi; Matthew Pavao

(57) ABSTRACT

Administration of a modulator of cell cycle checkpoint activation, which is preferably β-lapachone, or a pharmaceutically acceptable salt, prodrug, metabolite, analog or derivative thereof, protects normal cells against radiation injury. The invention includes methods of preventing radiation damage. The invention also provides methods for treating conditions such as cancer with radiotherapy, by administering a modulator of cell cycle checkpoint activation to a subject, prior to administration of radiotherapy.

20 Claims, 10 Drawing Sheets

OTHER PUBLICATIONS

Andreassen et al., "Chemical Radioprotection: A Critical Review of Amifostine as a Cytoprotector in Radiotherapy", *Seminars in Radiation Oncology*, 13(1):62-72 (2003).

Anzai et al.,"In Vivo Radioprotection of Mice by 3-Methyl-1-phenyl-2-pyrazolin-5-one (Edaravone; Radicut®), a Clinical Drug", *J. Radiat. Res.*, 45(2):319-323 (2004).

Ashwell et al., "Effect of Gamma Radiation on Resting B Lymphocytes II. Functional Characterization of the Antigen-Presentation Defect", *The Journal of Immunology*, 141(8):2536-2544 (1988).

Bonner et al., "New Dosing Regimens for Amifostine: A Pilot Study to Compare the Relative Bioavailability of Oral and Subcutaneous Administration with Intravenous Infusion", *J. Clin Pharmacol*, 42:166-174 (2002).

Boorstein et al., "β-Lapachone Greatly Enhances MMS Lethality to Human Fibroblasts", *Biochemical and Biophysical Research Communications*, 118(3):828-834 (1984).

Boothman et al., "Inhibition of Potentially Lethal DNA Damage Repair in Human Tumor Cells by β-Lapachone, an Activator of Topoisomerase 1", *Cancer Research*, 49(3):605-612 (1989).

Bourhis et al., "Radioprotective Effect of Amifostine in Patients With Head and Neck Squamous Cell Carcinoma", *Seminars in Oncology*, 29(6), Suppl. 19:61-62 (2002).

Cassatt et al., "Effects of Dose and Schedule on the Efficacy of Ethyol: Preclinical Studies", *Seminars in Oncology*, 30(6), Suppl. 18:31-39 (2003).

Cassatt et al., "Preclinical Studies on the Radioprotective Efficacy and Pharmacokinetics of Subcutaneously Administered Amifostine", *Seminars in Oncology*, 29(6), Suppl. 19:2-8 (2002).

Di Chenna et al., "Preparation and Cytotoxicity Toward Cancer Cells of Mono(arylimino) Derivatives of β-Lapachone", *J. Med. Chem.*, 44(15):2486-2489 (2001).

Douek et al., "Changes in Thymic Function with Age and During the Treatment of HIV Infection", *Nature*, 396:690-699 (1998).

Goncalves et al., "Evaluation of the Toxicity of 3-allyl-β-Lapachone Against *Trypanosoma Cruzi* Bloodstream Forms", *Molecular and Biochemical Parasitology*, 1(3):167-176 (1980).

Grdina et al., "Amifostine: Mechanisms of Action Underlying Cytoprotection and Chemoprevention", *Drug Metabolism and Drug Interactions*, 16(4):237-279 (2000).

Grdina et al., "Radioprotectants: Current Status and New Directions", *Oncology*, 63(suppl. 2):2-10 (2002).

Gupta et al., "An Unambiguous Synthesis of 4-Hydroxy-α-Lapachone & Its β-Isomer", *Indian Journal of Chemistry*, 16B(1):35-37 (1978).

Gupta et al., "Synthesis of 4-Hydroxy-α-Lapachone and Its β-Isomer", *Supplement to Current Science*, 46(10):337 (1977).

Han et al., "Gamma Irradiation-Reduced IFN-γ Expression, STAT1, Signals, and Cell-Mediated Immunity", *Journal of Biochemistry and Molecular Biology*, 35(6):583-589 (2002).

Li at al., "Induction of Apoptosis by β-Lapachone in Human Prostate Cancer Cells", *Cancer Research*, 55(17):3712-3715 (1995).

Li at al., "Induction of Apoptosis in Uninfected Lymphocytes by HIV-1 Tat Protein", *Science*, 268:429-431 (1995).

Li et al., "Potent Inhibition of Tumor Survival in vivo by β-Lapachone Plus Taxol: Combining Drugs Imposes Different Artificial Checkpoints", *PNAS*, 96(23):13369-13374 (1999).

Li et al., "Release of Mitochondrial Cytochrome C in Both Apoptosis and Necrosis Induced by β-Lapachone in Human Carcinoma Cells", *Molecular Medicine*, 5(4):232-239 (1999).

Li et al., "Selective Killing of Cancer Cells by β-Lapachone: Direct Checkpoint Activation as a Strategy Against Cancer", *PNAS*, 100(5):2674-2678 (2003).

MacVittie et al., "Therapeutic Use of Recombinant Human G-CSF (rhG-CSF) in a Canine Model of Sublethal and Lethal Whole-Body Irradiation", *Int. J. Radiat. Biol.*, 57(4):723-736 (1990).

Maruyama et al., "Syntheses of α- and β-Lapachones and Their Homologues By Way of Photochemical Side Chain Introduction to Quinone", *Chemistry Letters*, 8:847-850 (1977).

Mettler et al., "Major Radiation Exposure—What to Expect and How to Respond", *The New England Journal of Medicine*, 346(20):1554-1561 (2002).

Patchen et al., "Granulocyte Colony-Stimulating Factor and Amifostine (Ethyol) Synergize to Enhance Hemopoietic Reconstitution and Increase Survival in Irradiated Animals", *Seminars in Oncology*, 21(5), Suppl. 11:26-32 (1994).

Patchen et al., "Survival Enhancement and Hemopoietic Regeneration Following Radiation Exposure: Therapeutic Approach Using Glucan and Granulocyte Colony-Stimulating Factor", *Exp. Hematol.*, 18:1042-1048 (1990).

Patchen et al., "Therapeutic Administration of Recombinant Human Granulocyte Colony-Stimulating Factor Accelerates Hemopoietic Regeneration and Enhances Survival in a Murine Model of Radiation-Induced Myelosuppression", *International Journal of Cell Cloning*, 8:107-122 (1990).

Portela et al., "Redox Cycling of β-Lapachone and Related o-Naphthoquinones in the Presence of Dihydrolipoamide and Oxygen", *Biochemical Pharmacology*, 51:275-283 (1996).

V. Santini, "Amifostine: Chemotherapeutic and Radiotherapeutic Protective Effects", *Exp. Opin. Pharmacother.* 2(3):479-489 2001).

Schaffner-Sabba et al., "β-Lapachone: Synthesis of Derivatives and Activities in Tumor Models", *J. Med. Chem.*, 27(8):990-994 (1984).

Srinivasan et al., "Radioprotection, Pharmacokinetic and Behavioural Studies in Mouse Implanted with Biodegradable Drug (Amifostine) Pellets", *Int. J. Radiat. Biol.* 78(6):535-543 (2002).

Stickney et al., "HE2100 and HE3204 Protect Rhesus Macaques from Chemotherapy or Radiation Induced Myelosuppression", *Journal of Clinical Oncology*, 22(14S):599s, Abstract 6668 (2004).

Sun et al., "A Preparative Synthesis of Lapachol and Related Naphthoquinones", *Tetrahedron Letters*, 39:8221-8224 (1998).

Weiss et al., "Radioprotection by Antioxidants", *Annals of the New York Academy of Sciences*, 899:44-60 (2000).

Whitnall et al., "Protection Against γ-Irradiation with 5-Androstenediol", *Military Medicine*, 167:Suppl. 1:64-65 (2002).

Whitnall et al., "Radioprotective Efficacy and Acute Toxicity of 5-Androstenediol After Subcutaneous or Oral Administration in Mice", *Immunopharmacology and Immunotoxicology*, 24(4):595-626 (2002).

Workshop Draft Report: Molecular and Cellular Biology of Moderate Dose (1-10 Sv) Radiation and Potential Mechanisms of Radiation Protection, Bethesda, MD, pp. 1-45 (Dec. 17-18, 2001).

* cited by examiner

METHODS OF PROTECTING AGAINST RADIATION INJURY

CROSS REFERENCE TO RELATED APPLICATIONS

This application claims the benefit under 35 U.S.C. §119 (e) of U.S. Application No. 60/525,341, filed Nov. 26, 2003, and U.S. Application No. 60/561,901, filed Apr. 14, 2004, and U.S. Application No. 60/570,096, filed May 12, 2004, all of which applications are herein incorporated by reference in their entireties.

BACKGROUND OF THE INVENTION

Exposure to ionizing radiation (such as X-rays, gamma rays, and alpha- or beta-radiation) can cause damage to cells. This damage can result in cell death (e.g., through apoptosis), or can cause genetic changes in the cell, resulting in unchecked cell proliferation and cancer.

While, in general, exposure to such radiation is therefore undesirable, the administration of carefully monitored doses of radiation is an accepted treatment for certain cancers; by targeting the radiation to a tumor, cancer cells can be destroyed. A frequent complication of radiotherapy is the irradiation of normal tissues surrounding the cancerous tissues. Such normal tissues are often damaged by the radiation, resulting in undesired radiation injury to normal cells and tissues, which can have severe consequences for the affected patient.

Exposure to radiation can occur in several other ways, including exposure to normal background levels of radiation (such as cosmic rays or radiation due to naturally-occurring isotopes present in the earth) or elevated environmental radiation (including occupational exposure of workers in medical facilities or nuclear power plants). Another potential source of exposure to certain types of radiation is the accidental or intentional release of radioactive materials, for example, as the result of an accident or as a result of terrorist activity, e.g., as the result of a radiologic weapon such as a so-called "dirty bomb" (an explosive device intended to spread radioactive materials so as to contaminate an area).

The primary form of protection against radiation injury is avoidance of exposure to radiation. For example, shielding materials capable of preventing penetration of radiation into the body can be used when a source of radiation is known; e.g., lead aprons can be used to block x-rays. Protective clothing can be used to prevent contamination of the body with radioactive materials, and decontamination procedures can be used to remove radioactive materials.

Prophylactic treatment with iodine can be used to prevent accumulation of radioactive iodine in the thyroid gland, and thus to prevent radiation injury to the thyroid, but such treatment does not provide protection against other radioactive elements or other organ sites and cannot prevent injury once the radioactive isotope has delivered a dose of radiation to the tissue. Treatment with radioprotectants such as amifostine (an approved radioprotectant) is effective in preventing certain types of radiation damage, such as DNA damage due to free radicals (or other reactive species) produced by the radiation. However, the approved indications for amifostine are limited, and side-effects such as nausea have been noted.

Another compound, 5-androstenediol, has been tested as a radiation protectant in preclinical animal studies. This compound is reported to improve survival in mice exposed to radiation, possibly by stimulating production of neutrophils and other immune-system cells and thus preventing infection, a significant cause of death in radiation-injured subjects. However, this compound is a salvaging measure and it does not counteract the pathogenic mechanism of radiation nor protect organs other than the hematopoietic system. It has not yet been approved for human use.

While radiation injury and radiation sickness can be treated symptomatically, in most cases, it is difficult to prevent or ameliorate radiation damage or injury to cells once the exposure to radiation has occurred.

β-lapachone (3,4-dihydro-2,2-dimethyl-2H-naphtho[1,2-b]pyran-5,6-dione) is a simple non-water soluble orthonapthoquinone which can be isolated from the heartwood of the lapacho tree (See Hooker, S. C., (1936) *J. Am. Chem. Soc.* 58:1181-1190; Goncalves de Lima, O., et al., (1962) *Rev. Inst. Antibiot. Univ. Recife.* 4:3-17). The structure of β-lapachone was established by Hooker in 1896 and it was synthesized by Fieser in 1927 (Hooker, S. C., (1936) *J. Am. Chem. Soc.* 58:1181-1190).

β-lapachone has been shown to have a variety of pharmacological effects. Numerous derivatives have been synthesized and tested as anti-viral and anti-parasitic agents, and β-lapachone has been shown to have anti-trypanosomal effects (See Goncalves, A M et al. (1980) *Mol. Biochem. Parasitology* 1:167-176; Schaffner-Sabba, K. et al. (1984) *J. Med. Chem.* 27:990-994; Li, C J et al., (1993) *Proc. Natl. Acad. Sci. USA* 90:1839-1842). β-lapachone significantly prolongs the survival of mice infected with Rauscher leukemia virus, probably through inhibition of reverse transcriptase (Schaffner-Sabba, K. et al. (1984) *J. Med. Chem.* 27:990-994; Schuerch, A R et al., (1978 *Eur. J. Biochem.* 84:197-205). β-lapachone inhibits viral replication and gene expression directed by the long terminal repeat (LTR) of the human immunodeficiency virus type I (Li, C J et al., (1993) *Proc. Natl. Acad. Sci. USA* 90:1839-1842).

There have been reports that β-lapachone induces cell death in human prostate cancer cells (See Li, C J et al., 1 (1995) *Cancer Res.* 55:3712-3715) and that β-lapachone induces necrosis in human breast cancer cells, and apoptosis in ovary, colon, and pancreatic cancer cells mediated by caspase activation (Li, Y Z et al., (1999) *Molecular Medicine* 5:232-239). In addition, β-lapachone, when combined with paclitaxel (sold under the name Taxol® by Bristol-Myers Squibb Co., N.Y., N.Y.) at moderate doses, has effective anti-tumor activity in human ovarian, prostate and breast cancer xenograft models in nude mice (See Li, C J et al. (1999) *Proc. Natl. Acad. Sci. USA* 96:13369-13374).

β-lapachone was investigated as a sensitizer of cancer cells to ionizing radiation and DNA damaging agents (Boorstein, R J et al., (1984) *Biochem Biophys. Res. Commun.* 118:828-834; Boothman, et al., (1989) *Cancer Res.* 49:605-612). The combination of β-lapachone administration with X-ray irradiation was found to result in synergistic (increased) cytotoxicity in vitro in a human radioresistant malignant melanoma cell line; the authors of this report (Boothman, et al., (1989) *Cancer Res.* 49:605-612) suggest that β-lapachone inhibits the ability of the malignant cells to repair potential lethal DNA damage caused by the radiation.

The present inventors have now unexpectedly discovered that administration of a modulator of cell cycle checkpoint activation (e.g., an activator of a cell cycle checkpoint or checkpoints, such as β-lapachone) is effective for the protection of normal (e.g., non-cancerous) cells and organisms against radiation damage or injury, or the treatment of radiation damage or injury in normal cells and organisms, or both.

SUMMARY OF THE INVENTION

The present invention provides a method of preventing radiation injury, comprising administering to a subject in need thereof, prior to an exposure to radiation, a therapeutically effective amount of a modulator of cell cycle checkpoint activation, or a pharmaceutically acceptable salt, prodrug, metabolite, analog or derivative thereof, in combination with a pharmaceutically acceptable carrier, wherein the radiation injury is prevented.

The present invention provides a method of preventing radiation injury, comprising administering to a subject in need thereof, prior to an exposure to radiation, a therapeutically effective amount of β-lapachone, or a pharmaceutically acceptable salt, prodrug, metabolite, analog or derivative thereof, in combination with a pharmaceutically acceptable carrier, wherein the radiation injury is prevented.

The present invention also provides a method of treating radiation injury, comprising administering to a subject in need thereof, prior to an exposure to radiation, a therapeutically effective amount of a modulator of cell cycle checkpoint activation, or a pharmaceutically acceptable salt, prodrug, metabolite, analog or derivative thereof, in combination with a pharmaceutically acceptable carrier, wherein the radiation injury is treated.

The present invention also provides a method of treating radiation injury, comprising administering to a subject in need thereof, prior to an exposure to radiation, a therapeutically effective amount of β-lapachone, or a pharmaceutically acceptable salt, prodrug, metabolite, analog or derivative thereof, in combination with a pharmaceutically acceptable carrier, wherein the radiation injury is treated.

The present invention also provides a method of preventing radiation damage, comprising administering to a subject in need thereof, prior to an exposure to radiation, a therapeutically effective amount of a modulator of cell cycle checkpoint activation, or a pharmaceutically acceptable salt, prodrug, metabolite, analog or derivative thereof, in combination with a pharmaceutically acceptable carrier, wherein the radiation damage is prevented.

The present invention also provides a method of preventing radiation damage, comprising administering to a subject in need thereof, prior to an exposure to radiation, a therapeutically effective amount of β-lapachone, or a pharmaceutically acceptable salt, prodrug, metabolite, analog or derivative thereof, in combination with a pharmaceutically acceptable carrier, wherein the radiation damage is prevented.

The present invention provides a method of reducing an effect of radiation on normal cells in a subject at risk for incurring exposure to radiation, comprising administering to the subject prior to an exposure to radiation a therapeutically effective amount of a modulator of cell cycle checkpoint activation, or a pharmaceutically acceptable salt, prodrug, metabolite, analog or derivative thereof, wherein the effect of radiation on normal cells in the subject is reduced.

The present invention provides a method of reducing an effect of radiation on normal cells in a subject at risk for incurring exposure to radiation, comprising administering to the subject prior to an exposure to radiation a therapeutically effective amount of β-lapachone, or a pharmaceutically acceptable salt, prodrug, metabolite, analog or derivative thereof, wherein the effect of radiation on normal cells in the subject is reduced.

The present invention provides a method of reducing an effect of ionizing radiation on normal cells in a subject at risk for incurring exposure to ionizing radiation, comprising administering to the subject prior to an exposure to ionizing radiation a therapeutically effective amount of a modulator of cell cycle checkpoint activation, or a pharmaceutically acceptable salt, prodrug, metabolite, analog or derivative thereof, wherein the effect of ionizing radiation on normal cells in the subject is reduced.

The present invention provides a method of reducing an effect of ionizing radiation on normal cells in a subject at risk for incurring exposure to ionizing radiation, comprising administering to the subject prior to an exposure to ionizing radiation a therapeutically effective amount of β-lapachone, or a pharmaceutically acceptable salt, prodrug, metabolite, analog or derivative thereof, wherein the effect of ionizing radiation on normal cells in the subject is reduced.

The present invention also provides a method of reducing a subject's risk of developing cancer following an exposure to radiation comprising administering to a subject in need thereof prior to an exposure to ionizing radiation a therapeutically effective amount of a modulator of cell cycle checkpoint activation, or a pharmaceutically acceptable salt, prodrug, metabolite, analog or derivative thereof, wherein the subject's risk of developing cancer following said exposure to radiation is reduced.

The present invention also provides a method of reducing a subject's risk of developing cancer following an exposure to radiation comprising administering to a subject in need thereof prior to an exposure to ionizing radiation a therapeutically effective amount of β-lapachone, or a pharmaceutically acceptable salt, prodrug, metabolite, analog or derivative thereof, wherein the subject's risk of developing cancer following said exposure to radiation is reduced.

The present invention provides a method of preventing radiation injury to normal cells, comprising contacting a normal cell, prior to an exposure to radiation, with an effective amount of a modulator of cell cycle checkpoint activation, or a pharmaceutically acceptable salt, prodrug, metabolite, analog or derivative thereof, wherein the radiation injury is prevented.

The present invention provides a method of preventing radiation injury to normal cells, comprising contacting a normal cell, prior to an exposure to radiation, with an effective amount of β-lapachone, or a pharmaceutically acceptable salt, prodrug, metabolite, analog or derivative thereof, wherein the radiation injury is prevented.

The present invention provides a method of protecting non-cancerous cells against radiation injury, comprising contacting non-cancerous cells, prior to an exposure to radiation, with an effective amount of a modulator of cell cycle checkpoint activation, or a pharmaceutically acceptable salt, prodrug, metabolite, analog or derivative thereof, wherein the non-cancerous cells are protected against the radiation injury.

The present invention provides a method of protecting non-cancerous cells against radiation injury, comprising contacting non-cancerous cells, prior to an exposure to radiation, with an effective amount of β-lapachone, or a pharmaceutically acceptable salt, prodrug, metabolite, analog or derivative thereof, wherein the non-cancerous cells are protected against the radiation injury.

The present invention also provides a method of preventing radiation-induced cell death in non-cancerous cells, comprising contacting non-cancerous cells, prior to an exposure to radiation, with an effective amount of a modulator of cell cycle checkpoint activation, or a pharmaceutically acceptable salt, prodrug, metabolite, analog or derivative thereof, wherein the radiation-induced cell death of the non-cancerous cells is prevented.

The present invention also provides a method of preventing radiation-induced cell death in non-cancerous cells, comprising contacting non-cancerous cells, prior to an exposure to radiation, with an effective amount of β-lapachone, or a pharmaceutically acceptable salt, prodrug, metabolite, analog or derivative thereof, wherein the radiation-induced cell death of the non-cancerous cells is prevented.

The present invention provides a method of treating cancer, comprising a) administering to a subject in need thereof, in combination with radiation therapy, a therapeutically effective amount of a modulator of cell cycle checkpoint activation, or a pharmaceutically acceptable salt, prodrug, metabolite, analog or derivative thereof, wherein the therapeutically effective amount is sufficient to prevent radiation injury to normal cells; and b) administering to the subject an effective amount of radiation therapy to treat the cancer while preventing radiation injury to the normal cells, wherein the cancer is treated.

The present invention provides a method of treating cancer, comprising a) administering to a subject in need thereof, in combination with radiation therapy, a therapeutically effective amount of β-lapachone, or a pharmaceutically acceptable salt, prodrug, metabolite, analog or derivative thereof, wherein the therapeutically effective amount is sufficient to prevent radiation injury to normal cells; and b) administering to the subject an effective amount of radiation therapy to treat the cancer while preventing radiation injury to the normal cells, wherein the cancer is treated.

The present invention provides a method of treating cancer, comprising a) administering to a subject in need thereof, prior to radiation therapy, a therapeutically effective amount of a modulator of cell cycle checkpoint activation, or a pharmaceutically acceptable salt, prodrug, metabolite, analog or derivative thereof, wherein the therapeutically effective amount is sufficient to prevent radiation injury to normal cells; and b) administering to the subject an effective amount of radiation therapy to treat the cancer while preventing radiation injury to the normal cells, wherein the cancer is treated.

The present invention provides a method of treating cancer, comprising a) administering to a subject in need thereof, prior to radiation therapy, a therapeutically effective amount of β-lapachone, or a pharmaceutically acceptable salt, prodrug, metabolite, analog or derivative thereof, wherein the therapeutically effective amount is sufficient to prevent radiation injury to normal cells; and b) administering to the subject an effective amount of radiation therapy to treat the cancer while preventing radiation injury to the normal cells, wherein the cancer is treated.

The present invention provides a method of treating cancer, comprising a) administering to a subject in need thereof, prior to radiation therapy, a therapeutically effective amount of β-lapachone, or a pharmaceutically acceptable salt, prodrug, metabolite, analog or derivative thereof, wherein the therapeutically effective amount is sufficient to prevent radiation-induced cell death in non-cancerous cells; and b) administering to the subject an effective amount of radiation therapy to treat the cancer while preventing radiation-induced cell death in the non-cancerous cells, wherein the cancer is treated.

The present invention provides a method of treating cancer, comprising a) administering to a subject in need thereof, prior to radiation therapy, a therapeutically effective amount of a modulator of cell cycle checkpoint activation, or a pharmaceutically acceptable salt, prodrug, metabolite, analog or derivative thereof, wherein the therapeutically effective amount is sufficient to prevent radiation-induced cell death in non-cancerous cells; and b) administering to the subject an effective amount of radiation therapy to treat the cancer while preventing radiation-induced cell death in the non-cancerous cells, wherein the cancer is treated.

The present invention provides a kit for prevention of radiation injury, comprising a) a container comprising an effective amount of a modulator of cell cycle checkpoint activation, or a pharmaceutically acceptable salt, prodrug, metabolite, analog or derivative thereof, and b) instructions for using the a modulator of cell cycle checkpoint activation, or a pharmaceutically acceptable salt, prodrug, metabolite, analog or derivative thereof, prior to an exposure to radiation to prevent radiation injury in a subject.

The present invention provides a kit for prevention of radiation injury, comprising a) a container comprising an effective amount of β-lapachone, or a pharmaceutically acceptable salt, prodrug, metabolite, analog or derivative thereof, and b) instructions for using the β-lapachone, or a pharmaceutically acceptable salt, prodrug, metabolite, analog or derivative thereof, prior to an exposure to radiation to prevent radiation injury in a subject.

The present invention provides a kit for treatment of radiation injury, comprising a) a container comprising an effective amount of a modulator of cell cycle checkpoint activation, or a pharmaceutically acceptable salt, prodrug, metabolite, analog or derivative thereof, and b) instructions for using the β-lapachone, or a pharmaceutically acceptable salt, prodrug, metabolite, analog or derivative thereof, prior to an exposure to radiation to treat radiation injury in a subject.

The present invention provides a kit for treatment of radiation injury, comprising a) a container comprising an effective amount of β-lapachone, or a pharmaceutically acceptable salt, prodrug, metabolite, analog or derivative thereof, and b) instructions for using the β-lapachone, or a pharmaceutically acceptable salt, prodrug, metabolite, analog or derivative thereof, prior to an exposure to radiation to treat radiation injury in a subject.

The present invention provides a method of preventing radiation injury to normal cells, comprising a) contacting the normal cells with an effective amount of a modulator of cell cycle checkpoint activation or a pharmaceutically acceptable salt, prodrug, metabolite, analog or derivative thereof, and b) activating a cell cycle checkpoint within the normal cells, wherein the radiation injury is prevented.

The present invention provides a method of preventing radiation injury to normal cells, comprising a) contacting the normal cells with an effective amount of β-lapachone or a pharmaceutically acceptable salt, prodrug, metabolite, analog or derivative thereof, and b) activating a cell cycle checkpoint within the normal cells, wherein the radiation injury is prevented.

The present invention provides a method of preventing radiation injury to normal cells, comprising a) contacting the normal cells with an effective amount of a modulator of cell cycle checkpoint activation, or a pharmaceutically acceptable salt, prodrug, metabolite, analog or derivative thereof, and b) activating E2F1 within the normal cells, wherein the radiation injury is prevented.

The present invention provides a method of preventing radiation injury to normal cells, comprising a) contacting the normal cells with an effective amount of β-lapachone, or a pharmaceutically acceptable salt, prodrug, metabolite, analog or derivative thereof, and b) activating E2F1 within the normal cells, wherein the radiation injury is prevented.

The present invention provides a method of preventing radiation injury to normal cells, comprising a) contacting the normal cells with an effective amount of a modulator of cell cycle checkpoint activation, or a pharmaceutically acceptable salt, prodrug, metabolite, analog or derivative thereof, and b) activating BRCA1 within the normal cells, wherein the radiation injury is prevented.

The present invention provides a method of preventing radiation injury to normal cells, comprising a) contacting the normal cells with an effective amount of β-lapachone, or a pharmaceutically acceptable salt, prodrug, metabolite, analog or derivative thereof, and b) activating BRCA1 within the normal cells, wherein the radiation injury is prevented.

The present invention provides a method of preventing radiation injury to normal cells, comprising a) contacting the normal cells with an effective amount of a modulator of cell cycle checkpoint activation, or a pharmaceutically acceptable salt, prodrug, metabolite, analog or derivative thereof, and b) activating Chk2 within the normal cells, wherein the radiation injury is prevented.

The present invention provides a method of preventing radiation injury to normal cells, comprising a) contacting the normal cells with an effective amount of β-lapachone, or a pharmaceutically acceptable salt, prodrug, metabolite, analog or derivative thereof, and b) activating Chk2 within the normal cells, wherein the radiation injury is prevented.

The present invention provides a method of activating a cell cycle checkpoint pathway in a cancer cell, comprising contacting the cancer cell with an effective amount of a modulator of cell cycle checkpoint activation, or a pharmaceutically acceptable salt, prodrug, metabolite, analog or derivative thereof, wherein the contacting of the cancer cell results in activating the cell cycle checkpoint pathway in the cancer cell.

The present invention provides a method of activating a cell cycle checkpoint pathway in a cancer cell, comprising contacting the cancer cell with an effective amount of β-lapachone, or a pharmaceutically acceptable salt, prodrug, metabolite, analog or derivative thereof, wherein the contacting of the cancer cell results in activating the cell cycle checkpoint pathway in the cancer cell.

The present invention provides a method of activating a cell cycle checkpoint regulator in a cancer cell, comprising contacting the cancer cell with an effective amount of a modulator of cell cycle checkpoint activation, or a pharmaceutically acceptable salt, prodrug, metabolite, analog or derivative thereof, wherein the contacting of the cancer cell results in activating the cell cycle checkpoint regulator in the cancer cell.

The present invention provides a method of activating a cell cycle checkpoint regulator in a cancer cell, comprising contacting the cancer cell with an effective amount of β-lapachone, or a pharmaceutically acceptable salt, prodrug, metabolite, analog or derivative thereof, wherein the contacting of the cancer cell results in activating the cell cycle checkpoint regulator in the cancer cell.

The present invention provides a method of activating E2F1 in a cancer cell, comprising contacting the cancer cell with an effective amount of a modulator of cell cycle checkpoint activation, or a pharmaceutically acceptable salt, prodrug, metabolite, analog or derivative thereof, wherein the contacting of the cancer cell results in activating E2F1 in the cancer cell.

The present invention provides a method of activating E2F1 in a cancer cell, comprising contacting the cancer cell with an effective amount of β-lapachone, or a pharmaceutically acceptable salt, prodrug, metabolite, analog or derivative thereof, wherein the contacting of the cancer cell results in activating E2F1 in the cancer cell.

The present invention provides a method of activating an E2F1 checkpoint pathway in a cancer cell, comprising contacting the cancer cell with an effective amount of a modulator of cell cycle checkpoint activation, or a pharmaceutically acceptable salt, prodrug, metabolite, analog or derivative thereof, wherein the contacting of the cancer cell results in activating the E2F1 checkpoint pathway in the cancer cell.

The present invention provides a method of activating an E2F1 checkpoint pathway in a cancer cell, comprising contacting the cancer cell with an effective amount of β-lapachone, or a pharmaceutically acceptable salt, prodrug, metabolite, analog or derivative thereof, wherein the contacting of the cancer cell results in activating the E2F1 checkpoint pathway in the cancer cell.

The present invention provides a method of activating BRCA1 in a cancer cell, comprising contacting the cancer cell with an effective amount of a modulator of cell cycle checkpoint activation, or a pharmaceutically acceptable salt, prodrug, metabolite, analog or derivative thereof, wherein the contacting of the cancer cell results in activating BRCA1 in the cancer cell.

The present invention provides a method of activating BRCA1 in a cancer cell, comprising contacting the cancer cell with an effective amount of β-lapachone, or a pharmaceutically acceptable salt, prodrug, metabolite, analog or derivative thereof, wherein the contacting of the cancer cell results in activating BRCA1 in the cancer cell.

The present invention provides a method of activating Chk2 in a cancer cell, comprising contacting the cancer cell with an effective amount of a modulator of cell cycle checkpoint activation, or a pharmaceutically acceptable salt, prodrug, metabolite, analog or derivative thereof, wherein the contacting of the cancer cell results in activating Chk2 in the cancer cell.

The present invention provides a method of activating Chk2 in a cancer cell, comprising contacting the cancer cell with an effective amount of β-lapachone, or a pharmaceutically acceptable salt, prodrug, metabolite, analog or derivative thereof, wherein the contacting of the cancer cell results in activating Chk2 in the cancer cell.

The present invention provides a method of activating an ATM/ATR checkpoint pathway in a cancer cell, comprising contacting the cancer cell with an effective amount of a modulator of cell cycle checkpoint activation, or a pharmaceutically acceptable salt, prodrug, metabolite, analog or derivative thereof, wherein the contacting of the cancer cell results in activating the ATM/ATR checkpoint pathway in the cancer cell.

The present invention provides a method of activating a ATM/ATR checkpoint pathway in a cancer cell, comprising contacting the cancer cell with an effective amount of β-lapachone, or a pharmaceutically acceptable salt, prodrug, metabolite, analog or derivative thereof, wherein the contacting of the cancer cell results in activating the ATM/ATR checkpoint pathway in the cancer cell.

The present invention provides a method of activating a Chk2 checkpoint pathway in a cancer cell, comprising contacting the cancer cell with an effective amount of a modulator of cell cycle checkpoint activation, or a pharmaceutically acceptable salt, prodrug, metabolite, analog or derivative thereof, wherein the contacting of the cancer cell results in activating the Chk2 checkpoint pathway in the cancer cell.

The present invention provides a method of activating a Chk2 checkpoint pathway in a cancer cell, comprising contacting the cancer cell with an effective amount of β-lapachone, or a pharmaceutically acceptable salt, prodrug, metabolite, analog or derivative thereof, wherein the contacting of the cancer cell results in activating the Chk2 checkpoint pathway in the cancer cell.

The present invention provides a method of elevating the level of E2F1 in a cancer cell, comprising contacting the cancer cell with an effective amount of a modulator of cell cycle checkpoint activation, or a pharmaceutically acceptable salt, prodrug, metabolite, analog or derivative thereof, wherein the contacting of the cancer cell results in elevating the level of E2F1 in the cancer cell.

The present invention provides a method of elevating the level of E2F1 in a cancer cell, comprising contacting the cancer cell with an effective amount of β-lapachone, or a pharmaceutically acceptable salt, prodrug, metabolite, analog or derivative thereof, wherein the contacting of the cancer cell results in elevating the level of E2F1 in the cancer cell.

The present invention provides a method of elevating the level of BRCA1 in a cancer cell, comprising contacting the cancer cell with an effective amount of a modulator of cell cycle checkpoint activation, or a pharmaceutically acceptable salt, prodrug, metabolite, analog or derivative thereof, wherein the contacting of the cancer cell results in elevating the level of E2F1 in the cancer cell.

The present invention provides a method of elevating the level of BRCA1 in a cancer cell, comprising contacting the cancer cell with an effective amount of β-lapachone, or a pharmaceutically acceptable salt, prodrug, metabolite, analog or derivative thereof, wherein the contacting of the cancer cell results in elevating the level of E2F1 in the cancer cell.

The present invention provides a method of elevating the proportion of phosphorylated Chk2 in a cancer cell, comprising contacting the cancer cell with an effective amount of a modulator of cell cycle checkpoint activation, or a pharmaceutically acceptable salt, prodrug, metabolite, analog or derivative thereof, wherein the contacting of the cancer cell results in elevating the proportion of phosphorylated Chk2 in the cancer cell.

The present invention provides a method of elevating the proportion of phosphorylated Chk2 in a cancer cell, comprising contacting the cancer cell with an effective amount of β-lapachone, or a pharmaceutically acceptable salt, prodrug, metabolite, analog or derivative thereof, wherein the contacting of the cancer cell results in elevating the proportion of phosphorylated Chk2 in the cancer cell.

The present invention further provides a kit for the prevention of radiation injury or radiation damage, comprising a container comprising an effective amount of a modulator of cell cycle checkpoint activation, or a pharmaceutically acceptable salt, prodrug, metabolite, analog or derivative thereof, and instructions for using the modulator of cell cycle checkpoint activation to prevent radiation injury or radiation damage in a subject by administering the modulator of cell cycle checkpoint activation before exposure to radiation.

The present invention further provides a kit for the prevention of radiation injury or radiation damage, comprising a container comprising an effective amount of β-lapachone, or a pharmaceutically acceptable salt, prodrug, metabolite, analog or derivative thereof, and instructions for using the β-lapachone to prevent radiation injury or radiation damage in a subject by administering the β-lapachone before exposure to radiation.

The present invention further provides a kit for the prevention of radiation injury or radiation damage, comprising a container comprising an effective amount of a modulator of cell cycle checkpoint activation, or a pharmaceutically acceptable salt, prodrug, metabolite, analog or derivative thereof, and instructions for using the modulator of cell cycle checkpoint activation to prevent radiation injury or radiation damage in a subject by administering the modulator of cell cycle checkpoint activation immediately following exposure to radiation.

The present invention further provides a kit for the prevention of radiation injury or radiation damage, comprising a container comprising an effective amount of β-lapachone, or a pharmaceutically acceptable salt, prodrug, metabolite, analog or derivative thereof, and instructions for using the β-lapachone to prevent radiation injury or radiation damage in a subject by administering the β-lapachone immediately following exposure to radiation.

The present invention further provides a kit for treatment of radiation injury or radiation damage, comprising a container comprising an effective amount of a modulator of cell cycle checkpoint activation, or a pharmaceutically acceptable salt, prodrug, metabolite, analog or derivative thereof, and instructions for using the modulator of cell cycle checkpoint activation to treat radiation injury or radiation damage in a subject.

The present invention further provides a kit for treatment of radiation injury or radiation damage, comprising a container comprising an effective amount of β-lapachone, or a pharmaceutically acceptable salt, prodrug, metabolite, analog or derivative thereof, and instructions for using the β-lapachone to treat radiation injury or radiation damage in a subject.

The present invention further provides a kit for treatment of radiation injury or radiation damage, comprising a container comprising an effective amount of a modulator of cell cycle checkpoint activation, or a pharmaceutically acceptable salt, prodrug, metabolite, analog or derivative thereof, and instructions for using the modulator of cell cycle checkpoint activation to treat radiation injury or radiation damage in a subject by administering the modulator of cell cycle checkpoint activation immediately following exposure to radiation.

The present invention further provides a kit for treatment of radiation injury or radiation damage, comprising a container comprising an effective amount of β-lapachone, or a pharmaceutically acceptable salt, prodrug, metabolite, analog or derivative thereof, and instructions for using the β-lapachone to treat radiation injury or radiation damage in a subject by administering the β-lapachone immediately following exposure to radiation.

The present invention also provides a method for preventing radiation injury or radiation damage subsequent to an accidental or intentional release of radioactive materials, comprising administering to a subject in need thereof an effective amount of a modulator of cell cycle checkpoint activation, or a pharmaceutically acceptable salt, prodrug, metabolite, analog or derivative thereof, wherein the modulator of cell cycle checkpoint activation is administered prior to exposure of the subject to the accidental or intentional release of radioactive materials, and prevents the radiation injury or radiation damage in the subject.

The present invention also provides a method for preventing radiation injury or radiation damage subsequent to an accidental or intentional release of radioactive materials, comprising administering to a subject in need thereof an effective amount of β-lapachone, or a pharmaceutically acceptable salt, prodrug, metabolite, analog or derivative thereof, wherein the β-lapachone, or a pharmaceutically acceptable salt, prodrug, metabolite, analog or derivative thereof, is administered prior to exposure of the subject to the accidental or intentional release of radioactive materials, and prevents the radiation injury or radiation damage in the subject.

The present invention also provides a method for preventing radiation injury or radiation damage subsequent to an accidental or intentional release of radioactive materials, comprising administering to a subject in need thereof an effective amount of a modulator of cell cycle checkpoint activation, or a pharmaceutically acceptable salt, prodrug, metabolite, analog or derivative thereof, wherein the modulator of cell cycle checkpoint activation is administered immediately following exposure of the subject to the accidental or intentional release of radioactive materials, and prevents the radiation injury or radiation damage in the subject.

The present invention also provides a method for preventing radiation injury or radiation damage subsequent to an accidental or intentional release of radioactive materials, comprising administering to a subject in need thereof an effective amount of β-lapachone, or a pharmaceutically acceptable salt, prodrug, metabolite, analog or derivative thereof, wherein the β-lapachone, or a pharmaceutically acceptable salt, prodrug, metabolite, analog or derivative thereof, is administered immediately following exposure of the subject to the accidental or intentional release of radioactive materials, and prevents the radiation injury or radiation damage in the subject.

The present invention provides a method of treating a subject having cancer, comprising a) administering to the subject a modulator of cell cycle checkpoint activation, or a pharmaceutically acceptable salt, prodrug, metabolite, analog or derivative thereof, in an amount sufficient to protect normal cells from radiation damage, b) activating a cell cycle checkpoint within the patient, and c) administering to the subject an effective amount of radiation to treat the cancer while preventing radiation damage to normal cells.

The present invention provides a method of treating a subject having cancer, comprising a) administering to the subject β-lapachone, or a pharmaceutically acceptable salt, prodrug, metabolite, analog or derivative thereof, in an amount sufficient to protect normal cells from radiation damage, b) activating a cell cycle checkpoint within the patient, and c) administering to the subject an effective amount of radiation to treat the cancer while preventing radiation damage to normal cells.

The present invention also provides methods for preventing radiation injury to normal cells by administering a cell cycle checkpoint activator, or a pharmaceutically acceptable salt, prodrug, metabolite, analog or derivative thereof, to a subject prior to, or shortly after, exposure to radiation. The invention also provides to radiotherapy methods in which normal cells are protected from radiation injury by administration of a cell cycle checkpoint activator, or a pharmaceutically acceptable salt, prodrug, metabolite, analog or derivative thereof, prior to exposure to a therapeutic dose of radiation to the subject.

The present invention also provides methods for preventing radiation injury to normal cells by administering β-lapachone, or a pharmaceutically acceptable salt, prodrug, metabolite, analog or derivative thereof, to a subject prior to, or shortly after, exposure to radiation. The invention also provides to radiotherapy methods in which normal cells are protected from radiation injury by administration of β-lapachone, or a pharmaceutically acceptable salt, prodrug, metabolite, analog or derivative thereof, prior to exposure to a therapeutic dose of radiation to the subject.

The present invention also provides a method for preventing radiation damage or injury to normal cells or tissues. The method includes the step of administering an effective amount of a modulator of cell cycle checkpoint activation (such as β-lapachone or a derivative or analog thereof) to a subject, such that radiation damage or injury to normal cells or tissues is reduced (compared to untreated cells or tissues) or eliminated upon a subsequent exposure of the cells or tissues to radiation.

The present invention also provides a method of treating radiation damage or injury in a subject exposed to radiation. The method includes the step of administering to the subject an effective amount of a modulator of cell cycle checkpoint activation, such that radiation damage or injury is treated.

The present invention also provides a method of preventing death of radiation-damaged, or radiation-injured, non-cancerous cells. The method includes the step of contacting the radiation-damaged, or radiation-injured, non-cancerous cells with an effective amount of a modulator of cell cycle checkpoint activation, such that death of the radiation-damaged, or radiation-injured, non-cancerous cells is prevented.

The present invention also provides a method of preventing cancer in a subject exposed to radiation. The method includes the step of administering to the subject an effective amount of a modulator of cell cycle checkpoint activation, such that development of cancer in the subject is prevented.

The present invention also provides improved radiotherapy methods, e.g., radiotherapy for treatment of cancer. The methods include the step of administering to a subject an effective normal-cell-protecting amount of a modulator of cell cycle checkpoint activation (preferably β-lapachone or a derivatives or analog thereof) to a subject, and then administering to the subject an effective amount of radiation, such that radiation injury to normal cells is decreased or eliminated (compared to radiotherapy in the absence of the modulator of cell cycle checkpoint activation), and the subject is treated. In certain aspects, additional chemotherapeutic agents may also be administered to the subject.

The present invention also provides kits for the treatment or prevention of radiation injury. The kits comprise a container comprising an effective amount of a modulator of cell cycle checkpoint activation (preferably β-lapachone or a derivative or analog thereof), together with instructions for using the modulator of cell cycle checkpoint activation to prevent radiation injury to a subject (e.g., by administering the modulator of cell cycle checkpoint activation to a subject before exposure to radiation). In certain embodiments, the modulator of cell cycle checkpoint activation may be formulated together with a pharmaceutically acceptable carrier or diluent.

DETAILED DESCRIPTION OF THE INVENTION

Figure 1:
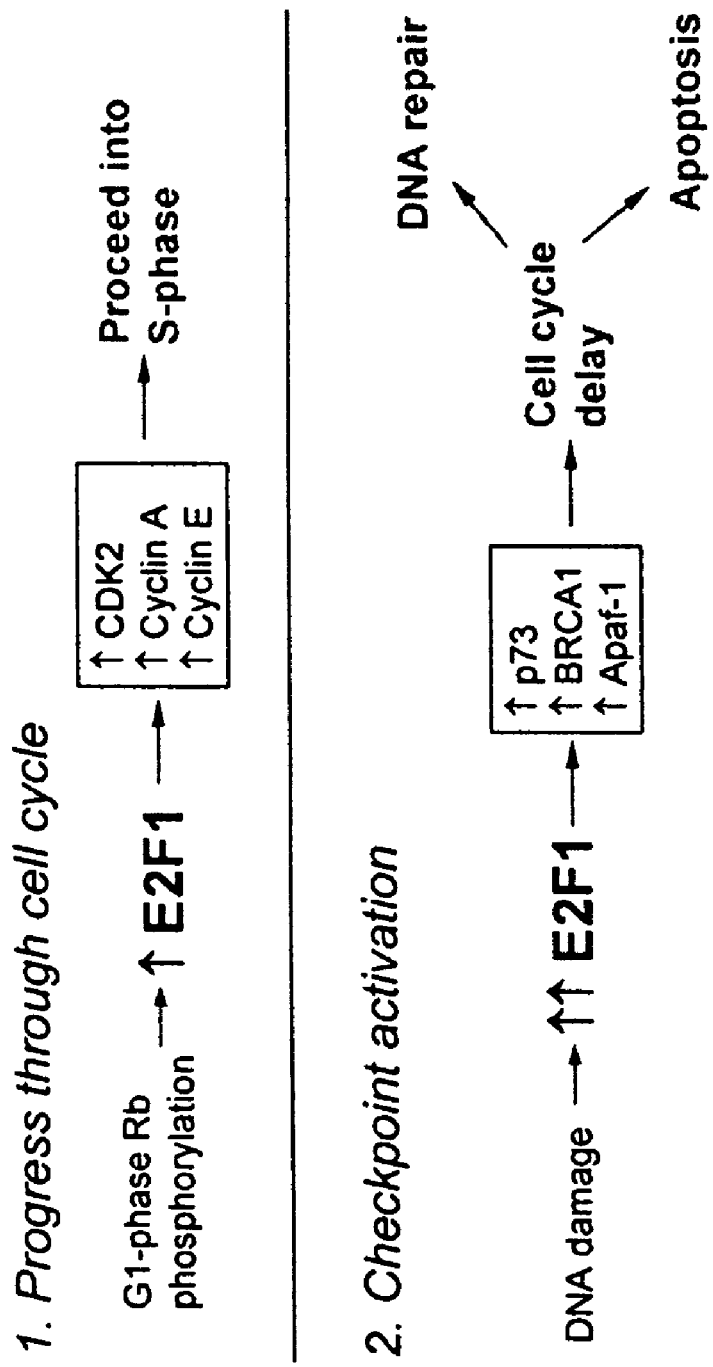
FIG. 1 is a schematic illustration of roles of E2F1 in the cell cycle and in checkpoint activation.

As used herein, the phrase "β-lapachone" refers to 3,4-dihydro-2,2-dimethyl-2H-naphtho[1,2-b]pyran-5,6-dione, represented by the chemical structure:

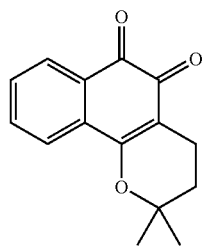

Preferred derivatives and analogs are discussed below.

While not limited by theory, the present invention includes and is based in part on an understanding of, and methods for, the activation of cell cycle checkpoints by modulators of cell cycle checkpoint activation (e.g., β-lapachone, or a pharmaceutically acceptable salt, prodrug, metabolite, analog or derivative thereof). The activation of cell cycle checkpoints in general is referred to as Activated Checkpoint Therapy™, or ACT™. ACT™ offers selectivity against cancer cells as compared to normal cells and is therefore safer than less selective therapies.

The term "modulator of cell cycle checkpoint activation," as used herein, refers to a compound capable of altering checkpoint activation in cells (in preferred embodiments, activating one or more cell cycle checkpoints), preferably by activating checkpoint-mediated DNA repair mechanisms, or by reinstating checkpoint activity that has been lost due to a malfunction or mutation in the cellular pathways that regulate cell cycle activity. As is known in the art, major cell cycle checkpoints occur at $G_1/S$ phase and at the $G_2/M$ phase transitions. In a model, four major cell cycle checkpoints monitor the integrity of genetic material. DNA synthesis begins only past the restriction point (R point), where the cell determines if preparation during G1 has been satisfactory for cell cycle continuation. The second checkpoint occurs during replication initiation in S phase. The third and fourth checkpoints take place in G2 phase and M phase, respectively. Modulation of cell cycle checkpoint activation is further discussed in, e.g., C. J. Li et al. *Proc. Natl. Acad. Sci. USA* (1999), 96(23), 13369-13374, and Y. Li et al. *Proc. Natl. Acad. Sci. USA* (2003), 100(5), 2674-2678, and PCT Publication WO 00/61142 (Pardee et al.). Preferred modulators of cell cycle checkpoint activation for use in the present invention induce checkpoint activation (i.e., activate one or more cell cycle checkpoints, preferably at $G_1/S$ phase), preferably without causing substantial DNA damage. In addition, certain preferred modulators of cell cycle checkpoint activation are capable of increasing the level or activity of E2F (more preferably E2F1) in a cell. Methods for screening for modulators of cell cycle checkpoint activation, including compounds capable of elevating E2F activity or levels in a cell, include those that are disclosed in PCT Patent Application No. PCT/US03/22631 to Li et al. In certain embodiments, preferred modulators of cell cycle checkpoint activation are capable of increasing the level or activity of E2F in a cell by an amount sufficient to cause apoptosis if the cell is a cancerous cell. More preferred modulators of cell cycle checkpoint activation are capable of raising the level or activity of E2F1 in a cell by an amount sufficient to cause apoptosis if the cell is a cancerous cell. More preferred modulators of cell cycle checkpoint activation are capable of increasing the level or activity of E2F1 in a cell by an amount sufficient to protect the cell from radiation injury or damage if the cell is a normal cell. In one aspect, a modulator of cell cycle checkpoint activation is not β-lapachone.

Again not limited by theory, cellular response to DNA damage is regulated by the ATM/ATR signal transduction pathway, in which ATM and ATR are protein kinases of the phosphatidyl-inositol-3 kinase family (PI3K). In response to DNA damage, ATM and ATR phosphorylate Chk2 and Chk1 respectively, which in turn activate a variety of substrates involved in arresting cells at the G1/S phase of the cell cycle, as well as inducing and activating proteins involved in DNA repair. Chk2 has been shown to activate proteins involved in DNA repair including the tumor suppressor BRCA1, thereby enhancing DNA repair capacity following DNA damage. Chk2 has also been shown to stabilize p53 both by directly phosphorylating p53, and by inhibiting Mdm2, a ubiquitin ligase that targets p53 for degradation. Under such conditions, increased levels of p53 lead to G1/S arrest, DNA repair, and apoptosis in cells with irreparable DNA damage. Again not limited by theory, it is believed that Chk2 is an important cell cycle regulator, which, depending on the conditions, can induce cell cycle arrest and DNA repair, or initiate apoptosis if DNA damage is too severe. In certain embodiments, preferred modulators of cell cycle checkpoint activation are capable of increasing the level or activity of Chk2 in a cell by an amount sufficient to cause apoptosis if the cell is a cancerous cell.

Again not limited by theory, E2F1 is one of related proteins in the E2F family of nuclear transcription factors, which family is critically important in regulation of the cell cycle. E2F1 is required for cellular proliferation by promoting passage through the G1/S checkpoint. During proliferation of normal cells, transcriptionally active E2F1 is liberated from an inactive E2F1/Rb complex following phosphorylation of Rb. E2F1 levels rise, promoting progression through G1. As the cell moves toward the end of S phase, E2F1 levels must decline for progress to continue. Sustained elevation of E2F1 at this point in the cell cycle causes activation of the S phase checkpoint, and subsequent cell death (e.g., by apoptosis). Thus, depending on the phase of the cell cycle and dynamics of E2F1 elevation, this regulatory protein may either promote cellular proliferation, induce cell cycle delay, DNA repair or cell death. As shown in FIG. 1, during the G1 phase of the cell cycle, phosphorylation of Rb results in dissociation of Rb-E2F1 complexes, liberating active E2F1, which then stimulates entry into S phase by promoting transcription of key cell cycle effectors. During S-phase, E2F1 must be degraded for progress to continue. In the presence of DNA damage, however, E2F1 levels increase rather than decrease, causing cell cycle delay, DNA repair, and, if damage is severe, cell death.

As used herein, "a cell cycle checkpoint pathway" refers to a biochemical pathway that is involved in modulation of a cell cycle checkpoint. A cell cycle checkpoint pathway may have stimulatory or inhibitory effects, or both, on one or more functions comprising a cell cycle checkpoint. A cell cycle checkpoint pathway is comprised of at least two compositions of matter, preferably proteins, both of which contribute to modulation of a cell cycle checkpoint. A cell cycle checkpoint pathway may be activated through an activation of one or more members of the cell cycle checkpoint pathway. Preferably, a cell cycle checkpoint pathway is a biochemical signaling pathway.

As used herein, "cell cycle checkpoint regulator" refers to a composition of matter that can function, at least in part, in modulation of a cell cycle checkpoint. A cell cycle checkpoint regulator may have stimulatory or inhibitory effects, or both, on one or more functions comprising a cell cycle checkpoint. In one aspect, a cell cycle checkpoint regulator is a protein. In another aspect, a cell cycle checkpoint regulator is a not a protein. In one aspect, a cell cycle checkpoint regulator is selected from the group consisting of ATM, ATR, Chk1, Chk2, E2F1, BRCA1, Rb, p53, p21, Mdm2, Cdc2, Cdc25, and 14-4-3[sigma].

In one aspect, administration to a subject in need thereof a modulator of cell cycle checkpoint activation results in activation of cell cycle checkpoints in normal cells. In another aspect, administration to a subject in need thereof a modulator of cell cycle checkpoint activation results in activation of cell cycle checkpoints in cells characterized by a cell proliferative disorder. In another aspect, administration to a subject in need thereof a modulator of cell cycle checkpoint activation results in activation of cell cycle checkpoints in cancer cells. In another aspect, administration to a subject in need thereof a modulator of cell cycle checkpoint activation results in activation of cell cycle checkpoints in normal cells and cancer cells. In yet another aspect, administration to a subject in need thereof a modulator of cell cycle checkpoint activation results in activation of cell cycle checkpoints in normal cells and cells characterized by a cell proliferative disorder. In another aspect, administration to a subject in need thereof a modulator of cell cycle checkpoint activation results in activation of cell cycle checkpoints in cancer cells and cells characterized by a cell proliferative disorder. In another aspect, administration to a subject in need thereof a modulator of cell cycle checkpoint activation results in activation of cell cycle checkpoints in normal cells, cancer cells, and cells characterized by a cell proliferative disorder.

Without wishing to be bound by any particular theory, it is believed that normal cells treated with a modulator of cell cycle checkpoint activation (such as an activator of a checkpoint) are advanced to a cell cycle checkpoint (e.g., the G1 or S phase checkpoint), thereby increasing levels of DNA repair enzymes and other components of a cell's repair mechanisms. (As noted above, cancerous cells, when treated with an effective amount of a modulator of cell cycle checkpoint activation such as β-lapachone, undergo apoptosis.) Such treated normal cells are therefore better able to repair any damage or injury caused by radiation than are untreated normal cells. Untreated normal cells do not immediately begin repairing radiation injury or damage, and this unrepaired damage can result in the accumulation of additional injury or damage (e.g., due to incorrectly synthesized DNA and RNA transcripts). While the untreated damaged cell will eventually reach a cell cycle checkpoint, the accumulated damage may be too great for the cell to repair, resulting in apoptosis of the cell. Treated normal cells are more likely to quickly repair any radiation injury or damage and avoid additional injury or damage, increasing the probability that the cell will survive. Again not limited by theory, activation of checkpoints by β-lapachone is believed to confer increased DNA repair capacity to lymphocytes, reduction of the radiosensitive proliferating fraction of mature and immature lymphocytes, and elimination of immune cells that are not repairable.

In one aspect, administration to a subject in need thereof an effective amount of a modulator of cell cycle checkpoint activation treats or prevents DNA damage in normal cells. In another aspect, administration to a subject in need thereof an effective amount of a modulator of cell cycle checkpoint activation results in increased cellular DNA repair activity in normal cells, or a decrease in detectable DNA damage in normal cells.

In one aspect, activating refers to placing one or more compositions of matter (e.g., protein or nucleic acid) in a state suitable for carrying out a desired biological function. In one aspect, a composition of matter capable of being activated also has an unactivated state. In one aspect, an activated composition of matter may have an inhibitory or stimulatory biological function, or both.

In one aspect, elevation refers to an increase in a desired biological activity of a composition of matter (e.g., a protein or a nucleic acid). In one aspect, elevation may occur through an increase in concentration of a composition of matter. In one aspect, elevating refers to an increase in a desired biological activity of a composition of matter (e.g., a protein or a nucleic acid).

As used herein, the term "selectively" means tending to occur at a higher frequency in one population than in another population. In one aspect, the compared populations are cell populations. In an aspect, a compound of the present invention selectively activates one molecular target (e.g., E2F1) but not on another molecular target (e.g., actin). In another preferred aspect, a compound of the present invention selectively elevates one molecular target (e.g., E2F1) but not on another molecular target (e.g., actin). In another aspect, a compound of the present invention selectively inhibits one molecular target but not on another molecular target. Preferably, an event occurs selectively in population A relative to population B if it occurs greater than two times more frequently in population A as compared to population B. More preferably, an event occurs selectively if it occurs greater than five times more frequently in population A. More preferably, an event occurs selectively if it occurs greater than ten times more frequently in population A; more preferably, greater than fifty times; even more preferably, greater than 100 times; and most preferably, greater than 1000 times more frequently in population A as compared to population B. For example, cell death would be said to occur selectively in cancer cells if it occurred greater than twice as frequently in cancer cells as compared to normal cells.

In a preferred aspect, a compound of the present invention (e.g., a modulator of cell cycle checkpoint activation, or a pharmaceutically acceptable salt, prodrug, metabolite, analog or derivative thereof) modulates an activity of a molecular target (e.g., E2F1). In one aspect, modulating refers to stimulating or inhibiting an activity of a molecular target. Preferably, a compound of the present invention modulates the activity of a molecular target if it stimulates or inhibits the activity of the molecular target by at least 2-fold relative to the activity of the molecular target under the same conditions but lacking only the presence of the compound. More preferably, a compound of the present invention modulates the activity of a molecular target if it stimulates or inhibits the activity of the molecular target by at least 4-fold, at least 8-fold, at least 10-fold, at least 20-fold, or at least 50-fold relative to the activity of the molecular target under the same conditions but lacking only the presence of the compound. The activity of a molecular target may be measured by any reproducible means. The activity of a molecular target may be measured in vitro or in vivo. For example, the activity of a molecular target may be measured in vitro by an enzymatic activity assay or a DNA binding assay, or the activity of a molecular target may be measured in vivo by assaying for expression of a reporter gene.

In one aspect, a compound of the present invention does not significantly modulate the activity of a molecular target if the addition of the compound does not stimulate or inhibit the activity of the molecular target by greater than 10% relative to the activity of the molecular target under the same conditions but lacking only the presence of the compound.

As used herein, the term "metabolite" means a product of metabolism of a modulator of cell cycle checkpoint activation, or a pharmaceutically acceptable salt, analog or derivative thereof, that exhibits a similar activity in vivo to a modulator of cell cycle checkpoint activation.

As used herein, the term "prodrug" means a compound of the present invention (e.g., a modulator of cell cycle checkpoint activation, or a pharmaceutically acceptable salt, metabolite, analog or derivative thereof) covalently linked to one or more pro-moieties, such as an amino acid moiety or other water solubilizing moiety. A compound of the present invention may be released from the pro-moiety via hydrolytic, oxidative, and/or enzymatic release mechanisms. In an embodiment, a prodrug composition of the present invention exhibits the added benefit of increased aqueous solubility, improved stability, and improved pharmacokinetic profiles. The pro-moiety may be selected to obtain desired prodrug characteristics. For example, the pro-moiety, e.g., an amino acid moiety or other water solubilizing moiety, may be selected based on solubility, stability, bioavailability, and/or in vivo delivery or uptake.

As used herein, the term "salt" is a pharmaceutically acceptable salt and can include acid addition salts including hydrochlorides, hydrobromides, phosphates, sulphates, hydrogen sulphates, alkylsulphonates, arylsulphonates, acetates, benzoates, citrates, maleates, fumarates, succinates, lactates, and tartrates; alkali metal cations such as Na, K, Li, alkali earth metal salts such as Mg or Ca, or organic amine salts.

As used herein, "contacting a cell" refers to a condition in which a compound or other composition of matter is in direct contact with a cell, or is close enough to induce a desired biological effect in a cell.

The term "subject," as used herein, refers to a mammal, including dog, cat, rat, mouse, monkey, cow, horse, goat, sheep, pig, camel, and, most preferably, a human. In a preferred embodiment, a subject is a human in need of treatment.

As used herein, a "subject in need thereof" is a subject in need of prophylaxis against, or treatment for, exposure to radiation. In certain embodiments, the subject can be a normal subject, e.g., a subject having no known or diagnosed abnormal cells, e.g., a cancer-free subject. In other embodiments (e.g., radiation therapy methods of the invention), the subject may be a subject having a cell proliferative disorder (e.g., cancer or a precancerous condition), or a subject having an increased risk of developing a cell proliferative disorder relative to the population at large.

In an embodiment, a subject to be treated by the present invention is at risk for incurring exposure to ionizing radiation. In one aspect, a subject is at risk for incurring exposure to ionizing radiation because the subject may be exposed to radiation in the course of employment (e.g., the employee is required to enter a site known or believed to be contaminated with radiation). In an aspect, a subject is at risk for incurring exposure to ionizing radiation in the course of performing tasks as an employee because the subject is employed by a nuclear facility, or because the subject is an emergency worker (e.g., firefighter or medical personnel) who will enter a site known or believed to be contaminated with radiation. In another aspect, a subject (e.g., a subject who is a civilian or a member of the military) is at risk for incurring exposure to radiation due to a credible risk of radiologic attack. In an aspect, a subject is at risk for incurring exposure to ionizing radiation in the course of performing tasks as a soldier.

As used herein, the term "cell proliferative disorder" refers to conditions in which unregulated or abnormal growth, or both, of cells can lead to the development of an unwanted condition or disease, which may or may not be cancerous. In one aspect, a cell proliferative disorder includes a precancer or a precancerous condition. In another aspect, a cell proliferative disorder includes cancer. In one aspect, a "precancer cell" or "precancerous cell" is a cell manifesting a cell proliferative disorder that is a precancer or a precancerous condition. In another aspect, a "cancer cell" or "cancerous cell" is a cell manifesting a cell proliferative disorder that is a cancer. Any reproducible means of measurement may be used to identify cancer cells or precancerous cells. In a preferred aspect, cancer cells or precancerous cells are identified by histological typing or grading of a tissue sample (e.g., a biopsy sample). In another aspect, cancer cells or precancerous cells are identified through the use of appropriate molecular markers. In one aspect, a cell proliferative disorder includes, for example, lung cancer and precancerous conditions of the lung. In one aspect, a cell proliferative disorder includes hyperplasia, metaplasia, and dysplasia.

As used herein, the term "normal cell" refers to a non-cancerous or non-hyperproliferating cell that is not pre-cancerous; thus, normal cells do not have DNA damage characteristic of cancerous or pre-cancerous cells. As used herein, a "normal cell" is a cell that cannot be classified as part of a "cell proliferative disorder." In one aspect, a normal cell lacks unregulated or abnormal growth, or both, that can lead to the development of an unwanted condition or disease. Preferably, a normal cell possesses normally functioning cell cycle checkpoint control mechanisms. As used herein, the term "non-cancerous cell" refers to a non-hyperproliferating cell that is not pre-cancerous and is not a cancer cell (i.e., is not cancerous).

As used herein, the terms "normal subject" or "healthy subject" refer to a subject not having cancer or other cell proliferative disorder. This invention provides methods and kits for treating or preventing radiation injury to cells, organs, or whole subjects.

As used herein, "monotherapy" refers to administration of a single active or therapeutic compound to a subject in need thereof. Preferably, monotherapy will involve administration of a therapeutically effective amount of an active compound. For example, cancer monotherapy with β-lapachone comprises administration of a therapeutically effective amount of β-lapachone to a subject in need of treatment of cancer. Monotherapy may be contrasted with combination therapy, in which a combination of multiple active compounds is administered, preferably with each component of the combination present in a therapeutically effective amount. In one aspect, monotherapy with a compound of the present invention (e.g., a modulator of cell cycle checkpoint activation, or a pharmaceutically acceptable salt, prodrug, metabolite, analog or derivative thereof) is more effective than combination therapy in inducing a desired biological effect.

As used herein, "therapeutically effective amount" means an amount of a drug or pharmaceutical agent that will elicit a desired biological or medical response of a tissue, system, animal or human that is being sought by a researcher or clinician. In one aspect, the biological or medical response is treatment of cancer. In another aspect, the biological or medical response is treatment or prevention of a cell proliferative disorder. In another aspect, the biological or medical response is treatment or prevention of radiologic injury or damage to normal cells and subjects.

The term "radiation," as used herein, refers to radiation, including ionizing radiation, capable of causing cellular damage. Such forms of radiation include alpha rays, beta rays, x-rays, gamma rays, and neutrons. In an aspect, ionizing radiation is radiation that has enough energy to eject electrons from electrically neutral atoms, leaving behind charged atoms or ions. In an aspect, ionizing radiation is a dose of radiation above 155 electron volts that may have carcinogenic, mutagenic, or teratogenic health effects in humans. In an aspect, alpha rays are alpha radiation or alpha particles (helium nuclei). In an aspect, beta rays are beta particles (electrons). In an aspect, high frequency electromagnetic waves, x-rays, are generally identical to gamma rays except for their place of origin. In an aspect, neutrons are not themselves ionizing but their collisions with nuclei lead to the ejection of other charged particles that do cause ionization. Other forms of radiation sufficiently energetic to cause damage to cells, such as ultraviolet (UV) radiation, are also included. Sources of radiation include radioactive isotopes, which may be naturally-occurring or manmade, and cosmic rays. Radiation can be emitted due to the gradual decay of radioactive isotopes, or due to nuclear fission or fusion events (as in an atomic bomb or nuclear reactor). In certain preferred embodiments, the radiation is x-ray radiation or gamma radiation. In other preferred embodiments, the radiation is beta radiation. In certain embodiments, the radiation is due to radiation therapy. In certain embodiments, the radiation is radiation due to radioactive fallout or contamination.

As used herein, "treating" describes the management and care of a patient for the purpose of combating a disease, condition, or disorder and includes the administration of a compound of the present invention to prevent the onset of symptoms or complications, alleviating the symptoms or complications, or eliminating the disease, condition or disorder.

The term "radiation damage," as used herein, refers to damage to a nucleic acid molecule in a cell, which damage is caused by exposure of the cell to radiation. For example, radiation exposure can result in double-strand breaks of nucleic acids. As another example, radiation exposure can result in single-strand nicks, breaks, or gaps in nucleic acids, as well as damage to, or loss of, nucleic acid bases. As another example, radiation exposure can result in nucleic acid translocations or various other chromosomal abnormalities. Radiation damage to nucleic acids may be direct or indirect, e.g., radiation may create free radicals, which in turn induce nucleic acid damage. As used herein, the term "preventing radiation damage" means eliminating, ameliorating or decreasing one or more indicia of radiation damage in a treated cell, compared to an untreated cell. As used herein, the term "protecting a cell or subject against radiation damage" means eliminating or decreasing one or more indicia of radiation damage in a treated cell compared to an untreated cell. In one aspect, preventing (or treating) radiation damage in a cell involves decreasing damage to one or more nucleic acid molecules in cells treated according to this invention by at least about 10% (more preferably 20%, 30%, 40%, 50%, 80%, 90%, or 95%), compared to untreated cells. In one aspect, preventing (or treating) radiation damage means enhancing DNA repair in a normal cell.

As used herein, the term "preventing radiation injury" means eliminating, ameliorating or decreasing one or more indicia or symptoms of radiation injury in a treated cell, organ or subject, or increasing survival of the subject, compared to an untreated cell, organ or subject. As used herein, the term "protecting a cell or subject against radiation injury" means eliminating or decreasing one or more indicia or symptoms of radiation injury in a treated cell or a subject, or increasing survival of the subject, compared to an untreated cell or subject. Symptoms or indicia of radiation injury in a cell are known in the art and include cell death by necrosis or apoptosis, or chromosomal damage. In preferred embodiments, preventing (or treating) radiation injury in a cell involves decreasing cell death in normal or non-cancerous cells treated according to this invention by at least about 10% (more preferably 20%, 30%, 40%, 50%, 80%, 90%, or 95%), compared to untreated cells. For example, decreasing cell death by 90% means that if n number of cells survive irradiation in a population of 1000 cells that are not treated with a compound of the present invention, then pretreatment of a equivalent population of 1000 cells with an effective amount of a compound of the present invention, followed by irradiation, will result in a surviving number of cells equal to $\{n+[(1000-n)*0.9]\}$. Number of cells in a population may be measured by any reproducible means. In one aspect, number of cells in a population is measured by fluorescence activated cell sorting (FACS). In another aspect, number of cells in a population is measured by immunofluorescence microscopy. In another aspect, number of cells in a population is measured by light microscopy. In another aspect, methods of measuring cell death are as shown in Li et al., (2003) *Proc Natl Acad Sci USA*. 100(5): 2674-8. In a preferred aspect, cell death results from apoptosis. Symptoms or indicia of radiation injury in a subject are known in the art and include both long-term and short-term effects, such as nausea, vomiting, hair loss, anemia, thrombocytopenia, leukopenia, loss of appetite, radiation burns, carcinogenesis (development or promotion of cancer) and death. In certain preferred embodiments, preventing (or treating) radiation injury in a subject involves decreasing death rates (e.g., mortality rates) in subjects treated according to this invention by at least about 10% (more preferably 20%, 30%, 40%, 50%, 80%, 90%, or 95%), compared to untreated subjects. In certain preferred embodiments, preventing (or treating) radiation injury in a subject involves increasing median survival time in subjects treated according to this invention by at least about 10% (more preferably 20%, 30%, 40%, 50%, 80%, 90%, or 95%), compared to untreated subjects. In certain preferred embodiments, preventing (or treating) radiation injury in a subject involves decreasing anemia in subjects treated according to this invention by at least about 10% (more preferably 20%, 30%, 40%, 50%, 80%, 90%, or 95%), compared to untreated subjects. In another embodiment, preventing (or treating) radiation injury in a subject involves decreasing the development, formation, or promotion of cancer in a treated subject by at least about 10% (more preferably 20%, 30%, 40%, 50%, 80%, 90%, or 95%), compared to untreated subjects. In another embodiment, preventing (or treating) radiation injury in a subject involves decreasing the development, formation, or promotion of cancer in a population of treated subjects by at least about 10% (more preferably 20%, 30%, 40%, 50%, 80%, 90%, or 95%), compared to untreated subjects. In another embodiment, preventing (or treating) radiation injury in a subject involves decreasing the rate of occurrence of an opportunistic infectious disease in a population of treated subjects by at least about 10% (more preferably 20%, 30%, 40%, 50%, 80%, 90%, or 95%), compared to untreated subjects.

In one aspect, prior to an exposure to radiation therapy for cancer, a subject may be given a therapeutically effective amount of a compound of the present invention that is sufficient to substantially prevent radiation injury to normal cells. In an aspect, a therapeutically effective amount is sufficient to substantially prevent radiation injury to normal cells if administering the compound results in decreasing cell death in normal or non-cancerous cells treated according to this invention by about 50% (more preferably, 60%, 70%, 80%, 90%, or 95%) compared to untreated cells. For example, decreasing cell death by 80% means that if n number of cells survive irradiation in a population of 1000 cells that are not treated with a compound of the present invention, then pre-treatment of an equivalent population of 1000 cells with an effective amount of a compound of the present invention, followed by irradiation, will result in a surviving number of cells equal to $\{n+[(1000-n)*0.8]\}$.

In one aspect, prior to, or in combination with, an exposure to radiation therapy for cancer, a subject may be given a therapeutically effective amount of a compound of the present invention that is sufficient to substantially prevent radiation-induced cell death in non-cancerous cells. In an aspect, a therapeutically effective amount is sufficient to substantially prevent radiation-induced cell death in non-cancerous cells if administering the compound results in decreasing cell death in non-cancerous cells treated according to this invention by about 50% (more preferably, 60%, 70%, 80%, 90%, or 95%) compared to untreated cells. For example, decreasing cell death by 80% means that if n number of cells survive irradiation in a population of 1000 cells that are not treated with a compound of the present invention, then pre-treatment of an equivalent population of 1000 cells with an effective amount of a compound of the present invention, followed by irradiation, will result in a surviving number of cells equal to $\{n+[(1000-n)*0.8]\}$.

Cells of the immune system, including neutrophils, are among the most radiosensitive in the body. In one aspect, symptoms or indicia of radiation injury include damage to the immune system or dysfunction of the immune system. As used herein, an "immune cell" is any cell that functions in an immune response or is a direct precursor to a cell that functions in an immune response, including but not limited to hematopoietic cells, lymphoid cells, myeloid cells, lymphocyte precursors, B cell precursors, T cell precursors, lymphocytes, B cells, T cells, plasma cells, monocytes, macrophages, neutrophils, eosinophils, basophils, natural killer cells (i.e., NK cells), mast cells, and dendritic cells. As used herein, a "white blood cell" (i.e., a leukocyte) is a blood cells that lacks hemoglobin, and includes but is not limited to lymphocytes, B cells, T cells, monocytes, macrophages, natural killer cells, neutrophils, eosinophils, and basophils. As used herein, a "lymphocyte" is type of white blood cell that is continuously made in the bone marrow, may be present in blood, lymph nodes, spleen, thymus, gut wall and bone marrow, and includes but is not limited to B lymphocytes and T lymphocytes. As used herein, a "monocyte" is a large white blood cell that is capable of phagocytosis and which, when it enters tissue, develops into a macrophage. As used herein a "neutrophil" is a white blood cell that is capable of phagocytosis and is distinguished by a lobed nucleus and granular cytoplasm. As used herein, a "natural killer cell" is a subset of bone marrow-derived lymphocytes, distinct from B or T cells, that function in innate immune responses through lytic mechanisms and by secreting IFN-γ. As used herein, a "spleen cell" is a cell found in, or originating from or acted upon by, the spleen and includes but is not limited to lymphocytes, red blood cells, splenic epithelial cells, dendritic cells, and macrophages. As used herein, a "thymus cell" is a cell found in, or originating from or acted upon by, the thymus and includes but is not limited to lymphocytes, stromal thymic epithelial cells, thymic cortical epithelial cells, thymic medullary epithelial cells, macrophages, dendritic cells, and T cell precursors.

In one aspect, radiation exposure induces leukopenia in a subject. As used herein, "leukopenia" is a condition in which the number of white blood cells circulating in the blood is reduced, e.g., a condition in which the white blood cell count (WBC) is below the normal range. In one aspect, in an adult human subject, a normal white blood cell count is between about 5,000 and 11,000 cu per microliter of whole blood. In one aspect, in an adult human subject, leukopenia exists when the white blood cell count is below about 5,000 cu per microliter. In another aspect, in an adult human subject, mild leukopenia exists when the white blood cell count is between about 3,000 and 5,000 cu per microliter, moderate leukopenia exists when the white blood cell count is between about 1,500 and 3,000 cu per microliter, and severe leukopenia exists when the white blood cell count is less than about 1,500 cu per microliter. White blood cell count may be measured by any reproducible means. In one aspect, a white blood cell count is measured by a medical diagnostic instrument capable of performing an automated white blood count.

In another aspect, radiation exposure induces neutropenia in a subject. As used herein, "neutropenia" is a condition in which the number of neutrophils circulating in the blood is reduced. In one aspect, in an adult human subject, a normal neutrophil count is between about 1,000 and 1,500 cells per $cc^3$ of whole blood. In one aspect, in an adult human subject, neutropenia exists when the neutrophil count is below about 1,000 cells per $cc^3$. In another aspect, in an adult human subject, mild neutropenia exists when the neutrophil count is between about 500 and 1,000 cells per $cc^3$, moderate neutropenia exists when the neutrophil count is between about 200 and 500 cells per $cc^3$, and severe neutropenia exists when the neutrophil count is less than about 200 cells per $cc^3$. Neutropenia may be assessed by any reproducible means. In one aspect, neutropenia is assessed by performing a white blood count and differential. In one aspect, a differential is performed by counting one hundred white blood cells and identifying them by shape and appearance of nucleus, color and granularity as either neutrophils, bands, lymphocytes, monocytes, eosinophils, basophils, or atypical or immature cells. In one aspect, a white blood cell count is measured by a medical diagnostic instrument capable of performing an automated white blood count. In one aspect, a differential is performed manually using a light microscope. In another aspect, a differential is performed automatically by a medical diagnostic instrument.

In another aspect, radiation exposure induces monocytopenia in a subject. As used herein, "monocytopenia" is a condition in which the number of monocytes circulating in the blood is reduced. In one aspect, in an adult human subject, a normal monocyte count is between about 40 and 180 cells per cc³ of whole blood. In one aspect, in an adult human subject, monocytopenia exists when the monocyte count is below about 35 cells per cc³. In another aspect, monocytopenia exists when the percentage of monocytes is less than about 2% using the differential assay method. Monocytopenia may be assessed by any reproducible means. In one aspect, monocytopenia is assessed by performing a white blood count and differential. In one aspect, a differential is performed by counting one hundred white blood cells and identifying them by shape and appearance of nucleus, color and granularity as either neutrophils, bands, lymphocytes, monocytes, eosinophils, basophils, or atypical or immature cells. In one aspect, a white blood cell count is measured by a medical diagnostic instrument capable of performing an automated white blood count. In one aspect, a differential is performed manually using a light microscope. In another aspect, a differential is performed automatically by a medical diagnostic instrument.

In another aspect, radiation exposure induces lymphocytopenia in a subject. As used herein, "lymphocytopenia" is a condition in which the number of lymphocytes circulating in the blood is reduced. In one aspect, in an adult human subject, a normal lymphocyte count is between about 400 and 1,200 cells per cc³ of whole blood. In one aspect, in an adult human subject, lymphocytopenia exists when the lymphocyte count is below about 350 cells per cc³. In another aspect, lymphocytopenia exists when the percentage of lymphocytes is less than about 20% using the differential assay method. Lymphocytopenia may be assessed by any reproducible means. In one aspect, lymphocytopenia is assessed by performing a white blood count and differential. In one aspect, a differential is performed by counting one hundred white blood cells and identifying them by shape and appearance of nucleus, color and granularity as either neutrophils, bands, lymphocytes, monocytes, eosinophils, basophils, or atypical or immature cells. In one aspect, a white blood cell count is measured by a medical diagnostic instrument capable of performing an automated white blood count. In one aspect, a differential is performed manually using a light microscope. In another aspect, a differential is performed automatically by a medical diagnostic instrument.

In another aspect, radiation exposure induces an altered profile of immune cells. In one aspect, an altered profile of immune cells may be assessed by performing a white blood count and differential. In one aspect, in an adult human subject, a normal profile of immune cells includes a total white cell count of between about 5,000 and 11,000 cu per microliter of whole blood; a neutrophil count of between about 1,000 and 1,500 cells per cc³ of whole blood; neutrophils 50-60%; lymphocytes 20-40%; monocytes 2-6%; eosinophils 1-4%; and basophils 0.5-1%. In one aspect, an altered profile of immune cells is a profile that differs from a normal profile in one of the stated parameters, or two, three, four, five, six or seven of the stated parameters. In one aspect, a white blood cell count is measured by a medical diagnostic instrument capable of performing an automated white blood count. In one aspect, a differential is performed manually using a light microscope. In another aspect, a differential is performed automatically by a medical diagnostic instrument.

In one aspect, administering an effective amount of a compound of the present invention prior to an exposure to radiation results in protecting the normal cellularity of the immune system. In an aspect, protecting the normal cellularity of the immune system means that the normal number and appearance of immune cells is maintained despite an exposure to radiation. Protecting the normal cellularity of the immune system may be measured by any reproducible means. In an embodiment, the normal cellularity of the immune system may be assessed quantitatively in a model organism (e.g., according to the methods described in Examples 7 and 8 herein). Preferably, maintaining the normal cellularity of the immune system means that administering an effective amount of a compound of the present invention prior to an exposure to radiation results in a change in the percentage of viable immune cells of most preferably less than 10%; or less preferably by less than 15%, less than 20%, less than 25%, less than 30%, or less than 40% in comparison to the average number of viable immune cells in an unirradiated matched control subject of the same species. In another embodiment, maintaining the normal cellularity of the immune system means that administering an effective amount of a compound of the present invention prior to an exposure to radiation results no visible qualitative difference in appearance of immune cells upon histological analysis of a spleen biopsy. In an aspect, qualitative difference in appearance of immune cells upon histological analysis may be measured by staining spleen sections with hematoxylin-eosin following standard procedures (e.g., according to the method described in Example 7c). In an aspect, maintaining the normal cellularity of the immune system may be measured by fluorescence activated cell sorting of immune cells.

In one aspect, administering an effective amount of a compound of the present invention prior to an exposure to radiation results in protecting the normal cellularity of the spleen. In an aspect, protecting the normal cellularity of the spleen means that the normal number and appearance of cells in the spleen is maintained despite an exposure to radiation. Protecting the normal cellularity of the spleen may be measured by any reproducible means. In an embodiment, the normal cellularity of the spleen may be assessed quantitatively in a model organism (e.g., according to the method described in Example 7b). Preferably, maintaining the normal cellularity of the spleen means that administering an effective amount of a compound of the present invention prior to an exposure to radiation results in a change in the percentage of viable spleen cells of most preferably less than 10%; or less preferably by less than 15%, less than 20%, less than 25%, less than 30%, or less than 40% in comparison to the average number of viable spleen cells in an unirradiated matched control subject of the same species. In another embodiment, maintaining the normal cellularity of the spleen means that administering an effective amount of a compound of the present invention prior to an exposure to radiation results no visible qualitative difference in appearance of spleen cells upon histological analysis of a spleen biopsy. In an aspect, qualitative difference in appearance of spleen cells upon histological analysis may be measured by staining spleen sections with hematoxylin-eosin following standard procedures (e.g., according to the method described in Example 7c).

In one aspect, administering an effective amount of a compound of the present invention prior to an exposure to radiation results in protecting the normal histology of an immune organ selected from the group consisting of thymus and spleen. Protecting the normal histology of an immune organ may be measured by any reproducible means (e.g., according to the methods described in Examples 7 and 8 herein).

In another aspect, administering an effective amount of a compound of the present invention results in protecting the normal histology of the spleen. In an aspect, protecting the normal histology of the spleen means that the spleen tissue appears qualitatively normal upon histological analysis despite an exposure to radiation. Protecting the normal histology of the spleen may be measured by any reproducible means. In an aspect, protecting the normal histology of the spleen may be measured by staining spleen sections with hematoxylin-eosin following standard procedures (e.g., according to the method described in Example 7c). In one aspect, administering an effective amount of a compound of the present invention prior to an exposure to radiation results in protecting the normal histology of an immune organ selected from the group consisting of thymus and spleen.

In another aspect, administering an effective amount of a compound of the present invention results in protecting the normal structure of the spleen. In an aspect, protecting the normal structure of the spleen means that the spleen structure appears qualitatively normal upon histological analysis despite an exposure to radiation. In an aspect, protecting the normal histology of the spleen may be measured by staining spleen sections with hematoxylin-eosin following standard procedures (e.g., according to the method described in Example 7c). In another aspect, protecting the normal structure of the spleen means that the spleen structure appears qualitatively normal upon macroscopically viewing the spleen, e.g., during a surgical examination of a subject, despite an exposure to radiation.

In another aspect, administering an effective amount of a compound of the present invention results in protecting the germinal centers of the spleen. In an aspect, protecting the germinal centers of the spleen means that the appearance of germinal centers appears qualitatively normal upon histological analysis despite an exposure to radiation. In an aspect, protecting the germinal centers of the spleen may be measured by staining spleen sections with hematoxylin-eosin following standard procedures (e.g., according to the method described in Example 7c).

In one aspect, administering an effective amount of a compound of the present invention prior to an exposure to radiation results in protecting the normal cellularity of the thymus. In an aspect, protecting the normal cellularity of the thymus means that the normal number and appearance of cells in the thymus is maintained despite an exposure to radiation. Protecting the normal cellularity of the thymus may be measured by any reproducible means. In an embodiment, the normal cellularity of the thymus may be assessed quantitatively in a model organism by any means of counting viable thymus cells (e.g., fluorescence activated cell sorting of viable cells). Preferably, maintaining the normal cellularity of the thymus means that administering an effective amount of a compound of the present invention prior to an exposure to radiation results in a change in the percentage of viable thymus cells of most preferably less than 10%; or less preferably by less than 15%, less than 20%, less than 25%, less than 30%, or less than 40% in comparison to the average number of viable thymus cells in an unirradiated matched control subject of the same species. In another embodiment, maintaining the normal cellularity of the thymus means that administering an effective amount of a compound of the present invention prior to an exposure to radiation results no visible qualitative difference in appearance of thymus cells upon histological analysis of a thymus biopsy. In an aspect, qualitative difference in appearance of thymus cells upon histological analysis may be measured by staining thymus sections with hematoxylin-eosin following standard procedures (e.g., according to the method described in Example 7a).

In another aspect, administering an effective amount of a compound of the present invention results in protecting the normal histology of the thymus. In an aspect, protecting the normal histology of the thymus means that the thymus tissue appears qualitatively normal upon histological analysis despite an exposure to radiation. Protecting the normal histology of the thymus may be measured by any reproducible means. In an aspect, protecting the normal histology of the thymus may be measured by staining thymus sections with hematoxylin-eosin following standard procedures (e.g., according to the method described in Example 7a).

In another aspect, administering an effective amount of a compound of the present invention results in protecting the normal structure of the thymus. In an aspect, protecting the normal structure of the thymus means that the thymus structure appears qualitatively normal upon histological analysis despite an exposure to radiation. In an aspect, protecting the normal histology of the thymus may be measured by staining thymus sections with hematoxylin-eosin following standard procedures (e.g., according to the method described in Example 7a). In another aspect, protecting the normal structure of the thymus means that the thymus structure appears qualitatively normal upon macroscopically viewing the thymus (e.g., during a surgical examination of a subject), despite an exposure to radiation.

In one aspect, administering an effective amount of a compound of the present invention results in decreasing cell death of thymus cells or spleen cells. In one aspect, administering an effective amount of a compound of the present invention results in decreasing cell death of normal thymus cells or non-cancerous thymus cells. aspect, administering an effective amount of a compound of the present invention results in decreasing cell death of normal spleen cells or non-cancerous spleen cells.

In one aspect, treating cancer results in a reduction in size of a tumor. A reduction in size of a tumor may also be referred to as "tumor regression." Preferably, after treatment, tumor size is reduced by 5% or greater relative to its size prior to treatment; more preferably, tumor size is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Size of a tumor may be measured by any reproducible means of measurement. In a preferred aspect, size of a tumor may be measured as a diameter of the tumor.

In another aspect, treating cancer results in a reduction in tumor volume. Preferably, after treatment, tumor volume is reduced by 5% or greater relative to its size prior to treatment; more preferably, tumor volume is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Tumor volume may be measured by any reproducible means of measurement.

In another aspect, treating cancer results in a decrease in number of tumors. Preferably, after treatment, tumor number is reduced by 5% or greater relative to number prior to treatment; more preferably, tumor number is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. Number of tumors may be measured by any reproducible means of measurement. In a preferred aspect, number of tumors may be measured by counting tumors visible to the naked eye or at a specified magnification. In a preferred aspect, the specified magnification is 2×, 3×, 4×, 5×, 10×, or 50×.

In another aspect, treating cancer results in an increase in average survival time of a population of treated subjects in comparison to a population receiving carrier alone. Preferably, the average survival time is increased by more than 30 days; more preferably, by more than 60 days; more preferably, by more than 90 days; and most preferably, by more than 120 days. An increase in average survival time of a population may be measured by any reproducible means. In a preferred aspect, an increase in average survival time of a population may be measured, for example, by calculating for a population the average length of survival following initiation of treatment with an active compound. In an another preferred aspect, an increase in average survival time of a population may also be measured, for example, by calculating for a population the average length of survival following completion of a first round of treatment with an active compound.

In another aspect, treating cancer results in an increase in average survival time of a population of treated subjects in comparison to a population of untreated subjects. Preferably, the average survival time is increased by more than 30 days; more preferably, by more than 60 days; more preferably, by more than 90 days; and most preferably, by more than 120 days. An increase in average survival time of a population may be measured by any reproducible means. In a preferred aspect, an increase in average survival time of a population may be measured, for example, by calculating for a population the average length of survival following initiation of treatment with an active compound. In an another preferred aspect, an increase in average survival time of a population may also be measured, for example, by calculating for a population the average length of survival following completion of a first round of treatment with an active compound.

In another aspect, treating cancer results in increase in average survival time of a population of treated subjects in comparison to a population receiving monotherapy with a drug that is not a compound of the present invention, or a pharmaceutically acceptable salt, prodrug, metabolite, analog or derivative thereof. Preferably, the average survival time is increased by more than 30 days; more preferably, by more than 60 days; more preferably, by more than 90 days; and most preferably, by more than 120 days. An increase in average survival time of a population may be measured by any reproducible means. In a preferred aspect, an increase in average survival time of a population may be measured, for example, by calculating for a population the average length of survival following initiation of treatment with an active compound. In an another preferred aspect, an increase in average survival time of a population may also be measured, for example, by calculating for a population the average length of survival following completion of a first round of treatment with an active compound.

In another aspect, treating cancer results in a decrease in the mortality rate of a population of treated subjects in comparison to a population receiving carrier alone. In another aspect, treating breast cancer results in a decrease in the mortality rate of a population of treated subjects in comparison to an untreated population. In a further aspect, treating breast cancer results a decrease in the mortality rate of a population of treated subjects in comparison to a population receiving monotherapy with a drug that is not a compound of the present invention, or a pharmaceutically acceptable salt, prodrug, metabolite, analog or derivative thereof. Preferably, the mortality rate is decreased by more than 2%; more preferably, by more than 5%; more preferably, by more than 10%; and most preferably, by more than 25%. In a preferred aspect, a decrease in the mortality rate of a population of treated subjects may be measured by any reproducible means. In another preferred aspect, a decrease in the mortality rate of a population may be measured, for example, by calculating for a population the average number of disease-related deaths per unit time following initiation of treatment with an active compound. In another preferred aspect, a decrease in the mortality rate of a population may also be measured, for example, by calculating for a population the average number of disease-related deaths per unit time following completion of a first round of treatment with an active compound.

In another aspect, treating cancer results in a decrease in tumor growth rate. Preferably, after treatment, tumor growth rate is reduced by at least 5% relative to number prior to treatment; more preferably, tumor growth rate is reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Tumor growth rate may be measured by any reproducible means of measurement. In a preferred aspect, tumor growth rate is measured according to a change in tumor diameter per unit time.

In another aspect, treating cancer results in a decrease in tumor regrowth. Preferably, after treatment, tumor regrowth is less than 5%; more preferably, tumor regrowth is less than 10%; more preferably, less than 20%; more preferably, less than 30%; more preferably, less than 40%; more preferably, less than 50%; even more preferably, less than 50%; and most preferably, less than 75%. Tumor regrowth may be measured by any reproducible means of measurement. In a preferred aspect, tumor regrowth is measured, for example, by measuring an increase in the diameter of a tumor after a prior tumor shrinkage that followed treatment. In another preferred aspect, a decrease in tumor regrowth is indicated by failure of tumors to reoccur after treatment has stopped.

In another aspect, treating or preventing a cell proliferative disorder results in a reduction in the rate of cellular proliferation. Preferably, after treatment, the rate of cellular proliferation is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The rate of cellular proliferation may be measured by any reproducible means of measurement. In a preferred aspect, the rate of cellular proliferation is measured, for example, by measuring the number of dividing cells in a tissue sample per unit time.

In another aspect, treating or preventing a cell proliferative disorder results in a reduction in the proportion of proliferating cells. Preferably, after treatment, the proportion of proliferating cells is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The proportion of proliferating cells may be measured by any reproducible means of measurement. In a preferred aspect, the proportion of proliferating cells is measured, for example, by quantifying the number of dividing cells relative to the number of nondividing cells in a tissue sample. In another preferred aspect, the proportion of proliferating cells is equivalent to the mitotic index.

In another aspect, treating or preventing a cell proliferative disorder results in a decrease in size of an area or zone of cellular proliferation. Preferably, after treatment, size of an area or zone of cellular proliferation is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Size of an area or zone of cellular proliferation may be measured by any reproducible means of measurement. In a preferred aspect, size of an area or zone of cellular proliferation may be measured as a diameter or width of an area or zone of cellular proliferation.

In another aspect, treating or preventing a cell proliferative disorder results in a decrease in the number or proportion of cells having an abnormal appearance or morphology. Preferably, after treatment, the number of cells having an abnormal morphology is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. An abnormal cellular appearance or morphology may be measured by any reproducible means of measurement. In one aspect, an abnormal cellular morphology is measured by microscopy, e.g., using an inverted tissue culture microscope. In one aspect, an abnormal cellular morphology takes the form of nuclear pleiomorphism.

I. Methods of Preventing or Treating Radiation Injury or Radiation Damage of Normal Cells, Tissues and Subjects The methods of the present invention are useful in several ways. In a first aspect, a modulator of cell cycle checkpoint activation (e.g., a G1/S-phase drug, such as β-lapachone, or a pharmaceutically acceptable salt, prodrug, metabolite, analog or derivative thereof) can be administered prior to, or concurrent with, exposure to radiation, to prevent radiation injury or damage to normal (e.g., non-cancerous) cells as a prophylactic treatment. Such prevention is useful where exposure to radiation can be predicted in advance and preparations can be made before the exposure occurs. For example, workers who may be exposed to radiation can be given a prophylactic dose of a modulator of cell cycle checkpoint activation before entering a contaminated site; soldiers can be given a prophylactic dose of a modulator of cell cycle checkpoint activation before entering a battlefield or other site that may be the target of a radiologic attack; civilians can be given a prophylactic dose of a modulator of cell cycle checkpoint activation in the event of a radiologic attack (or credible threat of such attack) on a civilian area.

If desired, e.g., to maintain prophylaxis over an extended period of time, repeated dosing (e.g., once daily, once every other day, or once weekly dosing) can be used. In addition, as described herein, a modulator of cell cycle checkpoint activation can be administered to a subject prior to administration to the subject of a therapeutic dose of radiation, to prevent damage to the subject's normal cells.

In a second aspect, a modulator of cell cycle checkpoint activation (e.g., a G1/S-phase drug) can be administered in the period after an exposure to radiation, to prevent radiation-induced damage or cell death that would occur without such treatment. In this case, the drug should preferably be administered to the subject before substantial cell death has occurred, preferably within, at most, 24 hours after exposure to the radiation, more preferably within 12 hours after exposure, more preferably within 8 hours after exposure, more preferably within 6 hours after exposure, yet more preferably within 4 hours after exposure, yet more preferably within 3 hours after exposure, yet more preferably within 2 hours after exposure, and still more preferably within one hour after exposure to radiation, more preferably within 30 minutes after exposure, more preferably within 20 minutes after exposure, more preferably within 10 minutes after exposure, even more preferably within 5 minutes after exposure, even more preferably within 2 minutes after exposure, and most preferably within 1 minute after exposure to radiation As used herein, an administration is "immediately following" an exposure to radiation if the administration occurs within 5 minutes after exposure to radiation.

In still another embodiment, the present invention provides a method for preventing radiation injury or damage subsequent to an accidental or intentional release of radioactive materials, comprising administering to a subject in need thereof an effective amount of a modulator of cell cycle checkpoint activation, where the modulator of cell cycle checkpoint activation is administered prior to, or immediately following, exposure of the subject to the accidental or intentional release of radioactive materials, and prevents the radiation injury or damage in the subject. In one aspect, workers who may be exposed to radiation during the cleanup of a radiologic accident at a nuclear plant can be given a prophylactic dose of a modulator of cell cycle checkpoint activation before entering a contaminated site. In another aspect, soldiers can be given a prophylactic dose of a modulator of cell cycle checkpoint activation before entering a battlefield or other site that may be the target of a radiologic attack. In another aspect, civilians can be given a prophylactic dose of a modulator of cell cycle checkpoint activation in the event of a radiologic attack, or credible threat of such attack, on a civilian area. For example, an intentional release of radioactive materials (e.g., radiologic attack) could include an explosion of a dirty bomb, an intentional explosion at a facility storing radioactive materials, an attack with a missile bearing a nuclear warhead, or any intentional release of materials capable of causing radiation-induced injuries to humans or other animals. In another aspect, civilians or soldiers who have been exposed to radiation following a radiologic accident at a nuclear plant, or a radiologic attack, can be given a therapeutic dose of a modulator of cell cycle checkpoint activation subsequent to exposure. In one aspect, an accidental or intentional release of radioactive materials involves a total body irradiation exposure of more than or equal to 50 mGy (5 Rads), 250 mGy (25 Rads), 0.5 Gy (50 Rads), 1 Gy (100 Rads), 1.5 Gy (150 Rads), 2.0 Gy (200 Rads), 2.5 Gy (250 Rads), 3.0 Gy (300 Rads), 3.5 Gy (350 Rads), 4.0 Gy (400 Rads), 5.0 Gy (500 Rads), 7.5 Gy (750 Rads), 10 Gy (1000 Rads) or 25 Gy (2500 Rads). Such exposure can be over a limited time span, for example, without limitation, between about 5 minutes and about 1 hour, between about 1 hour and about 24 hours, between about 24 hours and about 168 hours, between about 168 hours and about 744 hours, or between about 1 month and about 6 months.

In certain embodiments, the subject to be treated or protected is a normal subject and an effective amount of a compound of the present invention is administered prior to an exposure to radiation (e.g., ionizing radiation). In one aspect, the modulator of cell cycle checkpoint activation is administered to the subject to be treated or protected less than 24 hours prior to exposure of the subject to radiation, more preferably between 12 and 24 hours prior to exposure, more preferably between 8 and 12 hours prior to exposure, more preferably between 6 and 8 hours prior to exposure, more preferably between 4 and 6 hours prior to exposure, more preferably between 3 and 4 hours prior to exposure, more preferably between 2 and 3 hours prior to exposure, more preferably between 1 and 2 hours prior to exposure, more preferably between 0.5 and 1 hour prior to exposure, and more preferably between 0.25 and 0.5 hours prior to exposure. In another aspect, the modulator of cell cycle checkpoint activation is administered to the subject to be treated or protected between 10 and 15 minutes prior to exposure of the subject to radiation. In a preferred aspect, the modulator of cell cycle checkpoint activation is administered to the subject about 1 hour prior to radiation exposure. In another preferred aspect, the modulator of cell cycle checkpoint activation is administered to the subject about 0.5 hour prior to radiation exposure. In another aspect, the modulator of cell cycle checkpoint activation is administered to the subject to be treated or protected in a formulation enabling delayed release of the modulator of cell cycle checkpoint activation over an extended period of time. In such an aspect, the modulator of cell cycle checkpoint activation may be administered to the subject to be treated or protected about three months prior to exposure of the subject to radiation, between 2 and 3 months prior to exposure, between 1 and 2 months prior to exposure, between 3 and 4 weeks prior to exposure, between 2 and 3 weeks prior to exposure, between 1 and 2 weeks prior to exposure, between 3 and 7 days prior to exposure, or between 1 and 3 days prior to exposure. In certain embodiments, the modulator of cell cycle checkpoint activation may be formulated together with a pharmaceutically acceptable carrier or diluent.

In one aspect, the modulator of cell cycle checkpoint activation is administered to the cells to be treated or protected less than 24 hours prior to exposure of the cells to radiation, more preferably between 12 and 24 hours prior to exposure, more preferably between 8 and 12 hours prior to exposure, more preferably between 6 and 8 hours prior to exposure, more preferably between 4 and 6 hours prior to exposure, more preferably between 3 and 4 hours prior to exposure, more preferably between 2 and 3 hours prior to exposure, more preferably between 1 and 2 hours prior to exposure, more preferably between 0.5 and 1 hour prior to exposure, and more preferably between 0.25 and 0.5 hours prior to exposure. In another aspect, the modulator of cell cycle checkpoint activation is administered to the cells to be treated or protected between 10 and 15 minutes prior to exposure of the cells to radiation. In another aspect, the modulator of cell cycle checkpoint activation is administered to the cells to be treated or protected in a formulation enabling delayed release of the modulator of cell cycle checkpoint activation over an extended period of time. In such an aspect, the modulator of cell cycle checkpoint activation may be administered about three months prior to exposure of the cells to radiation, between 2 and 3 months prior to exposure, between 1 and 2 months prior to exposure, between 3 and 4 weeks prior to exposure, between 2 and 3 weeks prior to exposure, between 1 and 2 weeks prior to exposure, between 3 and 7 days prior to exposure, or between 1 and 3 days prior to exposure. In certain embodiments, the modulator of cell cycle checkpoint activation may be formulated together with a pharmaceutically acceptable carrier or diluent.

In an embodiment, the invention is directed to a method for preventing radiation damage or injury to normal (e.g., non-cancerous) cells or tissues. The method includes the step of administering an effective amount of a modulator of cell cycle checkpoint activation (such as β-lapachone, or a pharmaceutically acceptable salt, prodrug, metabolite, analog or derivative thereof) to a subject, such that radiation damage or injury to normal cells or tissues is reduced (compared to untreated cells or tissues) or eliminated upon a subsequent exposure of the cells or tissues to radiation. In a preferred embodiment, the modulator of cell cycle checkpoint activation is a compound capable of increasing E2F levels or activity in a cell. In a preferred embodiment, the modulator of cell cycle checkpoint activation is β-lapachone.

In an embodiment, the invention provides a method for protecting normal cells against radiation damage or injury, the method comprising the step of contacting the cells with an effective amount of a modulator of cell cycle checkpoint activation, prior to exposure of the cells to radiation. The methods of this embodiment of the invention may be useful in vivo or in vitro. In a preferred embodiment, the modulator of cell cycle checkpoint activation is a compound capable of increasing E2F levels or activity in a cell. In a preferred embodiment, the modulator of cell cycle checkpoint activation is β-lapachone.

In an embodiment, the invention is directed to a method for preventing radiation damage or injury in a subject. The method includes the step of administering to a subject in need thereof an effective amount of a modulator of cell cycle checkpoint activation prior to exposure of the subject to radiation. In a preferred embodiment, the modulator of cell cycle checkpoint activation is a compound capable of increasing E2F levels or activity in a cell. In a preferred embodiment, the modulator of cell cycle checkpoint activation is β-lapachone.

In an embodiment, the invention provides a method of preventing radiation damage or injury to normal cells in a healthy subject. The method includes the step of administering to the subject an effective amount of a modulator of cell cycle checkpoint activation, prior to exposure of the subject to radiation, such that radiation damage or injury to normal cells is prevented. In a preferred embodiment, the modulator of cell cycle checkpoint activation is a compound capable of increasing E2F levels or activity in a cell. In a preferred embodiment, the modulator of cell cycle checkpoint activation is β-lapachone.

In an embodiment, the invention provides a method of preventing death of radiation-damaged, or radiation-injured, non-cancerous cells, e.g., reducing the death rate or increasing survival time of radiation-damaged, or radiation-injured, non-cancerous cells. The method includes the step of contacting the radiation-damaged, or radiation-injured, non-cancerous cells (in vivo or in vitro) with an effective amount of a modulator of cell cycle checkpoint activation, such that death of the radiation-damaged, or radiation-injured, non-cancerous cells is prevented (or slowed). In a preferred embodiment, the modulator of cell cycle checkpoint activation is a compound capable of increasing E2F levels or activity in a cell. In a preferred embodiment, the modulator of cell cycle checkpoint activation is β-lapachone.

In an embodiment, the invention provides a method for treating radiation damage or injury in a subject exposed to radiation. The method includes the step of administering to a subject in need thereof (i.e., a subject already exposed to radiation) an effective amount of a modulator of cell cycle checkpoint activation after exposure of the subject to radiation. In a preferred embodiment, the modulator of cell cycle checkpoint activation is a compound capable of increasing E2F levels or activity in a cell. In a preferred embodiment, the modulator of cell cycle checkpoint activation is β-lapachone.

In an embodiment, the invention provides a method of preventing cancer in a subject exposed to radiation. The method includes the step of administering to the subject an effective amount of a modulator of cell cycle checkpoint activation, such that development of cancer (e.g., tumors) in the subject is prevented. In a preferred embodiment, the modulator of cell cycle checkpoint activation is a compound capable of increasing E2F levels or activity in a cell. In a preferred embodiment, the modulator of cell cycle checkpoint activation is β-lapachone.

II. Kits for Preventing or Treating Radiation Injury or Radiation Damage of Normal (e.g., Non-Cancerous) Cells, Tissues and Subjects In still another embodiment, the invention provides kits for preventing radiation damage or injury. The kits include a container comprising an effective amount of a modulator of cell cycle checkpoint activation (preferably β-lapachone) for preventing radiation damage or injury, together with instructions for administering the modulator of cell cycle checkpoint activation to a subject to prevent radiation damage or injury in the subject. In certain embodiments, the modulator of cell cycle checkpoint activation may be formulated together with a pharmaceutically acceptable carrier or diluent. In a preferred embodiment, a kit of the invention comprises an effective amount of a modulator of cell cycle checkpoint activation (preferably β-lapachone) in a formulation that can be rapidly administered to a large number of individuals. In another preferred embodiment, a kit of the invention comprises an effective amount of a modulator of cell cycle checkpoint activation (preferably β-lapachone) in a formulation that will be rapidly taken up by a subject's body such that a therapeutic effect is rapidly achieved. In one embodiment, a kit of the present invention comprises a modulator of cell cycle checkpoint activation (preferably β-lapachone) that is formulated for oral administration. In other embodiments, a kit of the present invention comprises a modulator of cell cycle checkpoint activation (preferably β-lapachone) that is formulated for intramuscular, intravenous, or pulmonary administration. In certain embodiments, a kit of the invention may include apparatus or devices useful for administration of the modulator of cell cycle checkpoint activation to the subject. For example, the kit can include applicators, needles and syringes for administration of a formulation intended for injection, or infusion sets for administration of a formulation intended for intravenous dosing.

The instructions included with the kit will preferably describe the appropriate indication, dosing schedule, and method of administration of the modulator of cell cycle checkpoint activation. The kits of the invention preferably have a suitably long shelf-life to permit stockpiling of sufficient quantities of drug in the event of future need.

For example, civil defense agencies could be supplied with the kits, facilitating rapid distribution of effective treatments for radiation damage or injury in the event of an actual or threatened radiological emergency. Similarly, military units could be equipped with the kits of the invention as part of standard-issue equipment for troops facing potential exposure to fallout or other radiologic hazards. For such kits, solid dosage forms may be preferred for reasons of stability. In preferred embodiments, the kit is storage-stable for a period of at least six months, more preferably at least one year, without loss of significant radioprotective efficacy (e.g., not more than a 10% decrease in efficacy). In preferred embodiments, the kit is storage-stable for a period of at least six months, more preferably at least one year, without loss of significant bioavailability (e.g., not more than a 10% decrease in bioavailability). In preferred embodiments, the kit is storage-stable for a period of at least six months, more preferably at least one year, without significant degradation of the active agent, i.e., the modulator of cell cycle checkpoint activation (e.g., not more than 10% degradation of the active agent).

III. Methods of Treatment of Cell Proliferative Disorders Including Cancer

The skilled artisan will appreciate that administration of a modulator of cell cycle checkpoint activation (such as β-lapachone) can have two complementary effects: first, protection of normal cells from radiation injury or damage; second, sensitization of cancer cells to radiation injury or damage. Thus, administration of such a compound to a subject prior to or in combination with radiation therapy can improve the selectivity of the radiation therapy for the cancer cells (that is, more cancer cells are killed, while fewer normal cells are killed, at a given dose of therapeutic radiation). This permits added flexibility in treatment.

In conventional radiotherapy methods, a medical provider (e.g., a radiation oncologist) determines a suitable dose of radiation to administer to a patient, based on factors such as the patient's weight, age, general physical condition, previous radio- or chemotherapy, and tumor size and type. In the improved radiotherapy methods of the invention, the medical provider may use a dose of radiation which differs from the dose that would be administered in a conventional course of radiotherapy. For example, the total dose of radiation administered can be reduced due to the sensitization of tumor cells to radiation, or the total amount of radiation administered can be increased (compared to the amount of radiation that would be administered to the patient in the absence of treatment with the modulator of cell cycle checkpoint activation) due to the improved resistance of normal cells to radiation injury or damage.

Thus, in a preferred embodiment, the invention provides improved methods of radiation therapy.

The methods comprise the steps of administering to a subject in need thereof, prior to administration of therapeutic radiation, an amount of a modulator of cell cycle checkpoint activation effective to protect normal cells from radiation injury or damage, and then administering therapeutic radiation to the subject, under conditions such that normal cells of the subject are protected from radiation injury, while targeted cells (such as cancer cells) are not protected from radiation injury (and preferably are sensitized to radiation injury). In an embodiment, the modulator of cell cycle checkpoint activation is a compound capable of increasing E2F levels in a cell. In a preferred embodiment, the modulator of cell cycle checkpoint activation is a compound capable of increasing E2F1 levels in a cell. In a preferred embodiment, the modulator of cell cycle checkpoint activation is β-lapachone.

In one aspect, the modulator of cell cycle checkpoint activation is administered to the subject less than 24 hours prior to exposure of the subject to radiation, more preferably between 12 and 24 hours prior to exposure, more preferably between 8 and 12 hours prior to exposure, more preferably between 6 and 8 hours prior to exposure, more preferably between 4 and 6 hours prior to exposure, more preferably between 3 and 4 hours prior to exposure, more preferably between 2 and 3 hours prior to exposure, more preferably between 1 and 2 hours prior to exposure, more preferably between 0.5 and 1 hour prior to exposure, and more preferably between 0.25 and 0.5 hours prior to exposure. In another aspect, the modulator of cell cycle checkpoint activation is administered to the subject between 10 and 15 minutes prior to exposure of the subject to radiation.

In another aspect, the modulator of cell cycle checkpoint activation is administered to the subject in a formulation enabling delayed release of the modulator of cell cycle checkpoint activation over an extended period of time. In such an aspect, the modulator of cell cycle checkpoint activation may be administered about three months prior to exposure of the subject to radiation, between 2 and 3 months prior to exposure, between 1 and 2 months prior to exposure, between 3 and 4 weeks prior to exposure, between 2 and 3 weeks prior to exposure, between 1 and 2 weeks prior to exposure, between 3 and 7 days prior to exposure, or between 1 and 3 days prior to exposure.

In another aspect, a modulator of cell cycle checkpoint activation is administered in the period after radiation therapy, to prevent radiation-induced damage or cell death that would occur without such treatment. In this case, the modulator of cell cycle checkpoint activation should preferably be administered to the subject before substantial cell death has occurred, preferably within, at most, 24 hours after exposure to the radiation, more preferably within 12 hours after exposure, more preferably within 8 hours after exposure, more preferably within 6 hours after exposure, yet more preferably within 4 hours after exposure, yet more preferably within 3 hours after exposure, yet more preferably within 2 hours after exposure, and still more preferably within one hour after exposure to radiation, more preferably within 30 minutes after exposure, more preferably within 20 minutes after exposure, more preferably within 10 minutes after exposure, even more preferably within 5 minutes after exposure, even more preferably within 2 minutes after exposure, and most preferably within 1 minute after exposure to radiation As used herein, an administration is "immediately following" an exposure to radiation if the administration occurs within 5 minutes after exposure to radiation.

The cancer should be a cancer treatable by radiation therapy, alone or in combination with a modulator of cell cycle checkpoint activation; in certain embodiments, the cancer is a hematologic cancer, such as multiple myeloma or leukemia; in other embodiments, the cancer is a solid tumor, such as prostate cancer, pancreatic cancer, lung cancer, ovarian cancer, uterine cancer, skin cancer (including melanoma), bone cancer, liver cancer, colon cancer, colorectal cancer, renal cancer, liver cancer, cancer of the brain, or breast cancer. In certain embodiments, the amount of radiation administered to the subject is greater than the amount of radiation that would have been administered to the subject in the absence of the modulator of cell cycle checkpoint activation; in preferred embodiments, the amount of radiation is increased by at least 10% (more preferably 20%, 50%, or 100%) over the amount of radiation that would have been administered to the subject in the absence of the modulator of cell cycle checkpoint activation. In other embodiments, the amount of radiation administered to the subject is less than the amount of radiation that would have been administered to the subject in the absence of the modulator of cell cycle checkpoint activation; in preferred embodiments, the amount of radiation is decreased by at least 10% (more preferably 20%, 50%, or 80%) relative to the amount of radiation that would have been administered to the subject in the absence of the modulator of cell cycle checkpoint activation. In certain embodiments, the amount of radiation administered to the subject is at a greater irradiation dose-rate than the irradiation dose-rate that would have been administered to the subject in the absence of the modulator of cell cycle checkpoint activation; in preferred embodiments, the irradiation dose-rate is increased by at least 10% (more preferably 20%, 50%, or 100%) over the irradiation dose-rate that would have been administered to the subject in the absence of the modulator of cell cycle checkpoint activation. In other embodiments, the amount of radiation administered to the subject is at a lesser irradiation dose-rate than the irradiation dose-rate that would have been administered to the subject in the absence of the modulator of cell cycle checkpoint activation; in preferred embodiments, the irradiation dose-rate is decreased by at least 10% (more preferably 20%, 50%, or 100%) over the irradiation dose-rate that would have been administered to the subject in the absence of the modulator of cell cycle checkpoint activation. In one aspect, radiation dose-rate is measured in units of Gy/min. In certain embodiments, the modulator of cell cycle checkpoint activation may be formulated together with a pharmaceutically acceptable carrier or diluent. In one aspect, a compound of the present invention is administered to a subject in need thereof in combination with radiation therapy for cancer.

In one aspect, the present invention provides a method of treating cancer, comprising a) administering to a subject in need thereof, prior to radiation therapy, a therapeutically effective amount of a modulator of cell cycle checkpoint activation, or a pharmaceutically acceptable salt, prodrug, metabolite, analog or derivative thereof, where the therapeutically effective amount is sufficient to prevent radiation injury to normal cells; and b) administering to the subject an effective amount of radiation therapy to treat the cancer while preventing radiation injury to the normal cells, where the cancer is treated.

In one aspect, the present invention provides a method of treating cancer, comprising a) administering to a subject in need thereof, prior to radiation therapy, a therapeutically effective amount of β-lapachone, or a pharmaceutically acceptable salt, prodrug, metabolite, analog or derivative thereof, where the therapeutically effective amount is sufficient to prevent radiation injury to normal cells; and b) administering to the subject an effective amount of radiation therapy to treat the cancer while preventing radiation injury to the normal cells, where the cancer is treated.

In one aspect, the present invention provides a method of treating cancer, comprising a) administering to a subject in need thereof, prior to radiation therapy, a therapeutically effective amount of a modulator of cell cycle checkpoint activation, or a pharmaceutically acceptable salt, prodrug, metabolite, analog or derivative thereof, where the therapeutically effective amount is sufficient to prevent radiation-induced cell death in non-cancerous cells; and b) administering to the subject an effective amount of radiation therapy to treat the cancer while preventing radiation-induced cell death in the non-cancerous cells, where the cancer is treated.

In one aspect, the present invention provides a method of treating cancer, comprising a) administering to a subject in need thereof, prior to radiation therapy, a therapeutically effective amount of β-lapachone, or a pharmaceutically acceptable salt, prodrug, metabolite, analog or derivative thereof, where the therapeutically effective amount is sufficient to prevent radiation-induced cell death in non-cancerous cells; and b) administering to the subject an effective amount of radiation therapy to treat the cancer while preventing radiation-induced cell death in the non-cancerous cells, where the cancer is treated.

In another aspect, the invention provides method of treating a subject having cancer, the method comprising the steps of a) administering to the subject an amount of a modulator of cell cycle checkpoint activation sufficient to protect normal cells from radiation damage or injury; and b) administering to the subject an effective amount of radiation to the subject to treat the cancer while substantially preventing radiation damage or injury to normal cells.

In another aspect, the invention provides method of treating a subject having cancer, the method comprising the steps of a) administering to the subject an amount of a modulator of cell cycle checkpoint activation sufficient to protect normal cells from radiation damage or injury; and b) administering to the subject an effective amount of radiation to the subject to treat the cancer while significantly preventing radiation damage or injury to normal cells.

The present invention also provides a method of treating cancer cells, comprising administering to one or more cells an amount of a modulator of cell cycle checkpoint activation sufficient to protect normal cells from radiation damage; and administering to the cells an effective amount of radiation to treat the cancer cells while substantially preventing the radiation damage to normal cells.

In one aspect, the invention provides a method of treating a cell proliferative disorder, comprising a) administering to a subject in need thereof a therapeutically effective amount of β-lapachone, or a pharmaceutically acceptable salt, prodrug, metabolite, analog or derivative thereof, wherein the therapeutically effective amount is sufficient to prevent radiation injury to normal cells; and b) administering to the subject an effective amount of radiation therapy to treat the cell proliferative disorder while preventing radiation injury to the normal cells, wherein the cell proliferative disorder is treated. In a preferred aspect, the cell proliferative disorder is a cell proliferative disorder of the skin or immune system. In another preferred aspect, the radiation therapy comprises radiation therapy with ultraviolet light. In an aspect, the cell proliferative disorder is psoriasis.

IV. Useful Modulators of Cell Cycle Checkpoint Activation and Their Administration Preferred G1 and/or S phase checkpoint activating compounds include G1/S phase drugs (for example, β-lapachone, and derivatives and analogs thereof, including reduced β-lapachone), and G1 phase drugs (for example, lovastatin, mimosine, tamoxifen, and the like). β-lapachone, and its derivatives and analogs (e.g., as described below), including reduced β-lapachone (Formula Ia, most preferably in which R' and R" are both hydrogen) and compounds of Formula VI, are more preferred, and β-lapachone is most preferred.

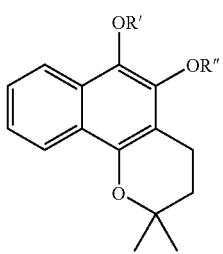

Formula Ia

One modulator of cell cycle checkpoint activation is β-lapachone. β-lapachone is well tolerated in dogs, rats, mice, and chickens. The maximum tolerated dose, when given p.o. daily for one month, is 200 mg/kg in rats, and 100 mg/kg in dogs. Of course, the appropriate dose for a given subject will vary depending on the species of the subject, the health of the subject, the route of administration (e.g., oral, intravenous, and the like) and other factors that are known to one of skill in the art.

Preferably, a compound (such as β-lapachone or a derivative or analog thereof) is administered to a patient in at least one dose in the range of 100 to 500,000 µg per kilogram body weight of recipient per day, more preferably in the range of 1000 to 250,000 µg per kilogram body weight per day, most preferably in the range of 10000 to 150,000 µg per kilogram body weight per day. Doses can also be expressed in units of mg/m$^2$; as an example, a suitable dose for a human subject is preferably in the range of 2 mg/m$^2$ to 5000 mg/m$^2$, more preferably 20 mg/m$^2$ to 500 mg/m$^2$ (still more preferably 30 to 300 mg/m$^2$) when dosage is by intravenous infusion once weekly. The desired dose is suitably administered once or in several more sub-doses administered at appropriate intervals (e.g., once per week, once per day, divided doses administered throughout the day, or other appropriate schedule).

These sub-doses may be administered as unit dosage forms, for example, containing 1 to 20,000 µg, preferably 10 to 10,000 µg per unit dosage form. Repeated doses can be administered as appropriate, e.g., to maintain a protective effect against continuing exposure (or potential exposure) to radiation.

As mentioned above, preferred modulators of cell cycle checkpoint activation for use in the present invention induce checkpoint activation, preferably without causing substantial DNA damage. In addition, preferred modulators of cell cycle checkpoint activation are capable of increasing the level or activity of E2F (more preferably E2F1) in a cell. Methods for screening for modulators of cell cycle checkpoint activation, including compounds capable of elevating E2F activity or levels in a cell, include methods such as those disclosed in PCT Patent Application No. PCT/US03/22631 (WO 04/07531) to Li et al. Assays for determining cell death or survival are also disclosed in PCT Patent Application No. PCT/US03/22631; such assays are useful for determining compounds effective to prevent cell death after exposure to radiation.

In light of the teachings herein, one of ordinary skill in the art will be able to screen potential modulators of cell cycle checkpoint activation to determine which compounds are useful in the methods and kits of the present invention, using no more than routine experimentation.

While β-lapachone is a suitable compound for use in the composition in accordance with the present invention, the invention is not limited in this respect, and β-lapachone derivatives or analogs, such as lapachol, and pharmaceutical compositions and formulations thereof are part of the present invention. Such β-lapachone analogs include, without limitation, those recited in PCT International Application PCT/US93/07878 (WO 94/04145), which discloses compounds of the formula:

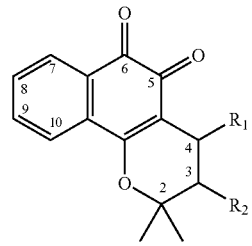

where R and $R_1$ are each independently hydrogen, substituted and unsubstituted aryl, substituted and unsubstituted alkenyl, substituted and unsubstituted alkyl and substituted or unsubstituted alkoxy. The alkyl groups preferably have from 1 to about 15 carbon atoms, more preferably from 1 to about 10 carbon atoms, still more preferably from 1 to about 6 carbon atoms. The term alkyl unless otherwise modified refers to both cyclic and noncyclic groups, although of course cyclic groups will comprise at least three carbon ring members. Straight or branched chain noncyclic alkyl groups are generally more preferred than cyclic groups. Straight chain alkyl groups are generally more preferred than branched. The alkenyl groups preferably have from 2 to about 15 carbon atoms, more preferably from 2 to about 10 carbon atoms, still more preferably from 2 to 6 carbon atoms. Especially preferred alkenyl groups have 3 carbon atoms (i.e., 1-propenyl or 2-propenyl), with the allyl moiety being particularly preferred. Phenyl and napthyl are generally preferred aryl groups. Alkoxy groups include those alkoxy groups having one or more oxygen linkage and preferably have from 1 to 15 carbon atoms, more preferably from 1 to about 6 carbon atoms. The substituted R and $R_1$ groups may be substituted at one or more available positions by one or more suitable groups such as, for example, alkyl groups such as alkyl groups having from 1 to 10 carbon atoms or from 1 to 6 carbon atoms, alkenyl groups such as alkenyl groups having from 2 to 10 carbon atoms or 2 to 6 carbon atoms, aryl groups having from six to ten carbon atoms, halogen such as fluoro, chloro and bromo, and N, O and S, including heteroalkyl, e.g., heteroalkyl having one or more hetero atom linkages (and thus including alkoxy, aminoalkyl and thioalkyl) and from 1 to 10 carbon atoms or from 1 to 6 carbon atoms.

Other β-lapachone analogs contemplated in accordance with the present invention include those described in U.S. Pat. No. 6,245,807, which discloses β-lapachone analogs and derivatives having the structure:

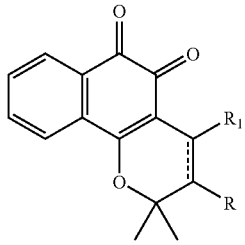

where R and $R_1$ are each independently selected from hydrogen, hydroxy, sulfhydryl, halogen, substituted alkyl, unsubstituted alkyl, substituted alkenyl, unsubstituted alkenyl, substituted aryl, unsubstituted aryl, substituted alkoxy, unsubstituted alkoxy, and salts thereof, where the dotted double bond between the ring carbons represents an optional ring double bond.

Additional β-lapachone analogs and derivatives are recited in PCT International Application PCT/US00/10169 (WO00/61142), which discloses compounds of the structure:

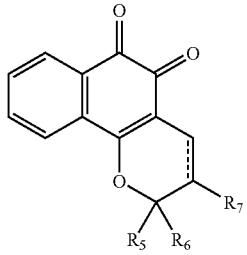

where $R_5$ and $R_6$ may be independently selected from hydroxy, $C_1$-$C_6$ alkyl, $C_1$-$C_6$ alkenyl, $C_1$-$C_6$ alkoxy, $C_1$-$C_6$ alkoxycarbonyl, —$(CH_2)_n$-phenyl; and $R_7$ is hydrogen, hydroxyl, $C_1$-$C_6$ alkyl, $C_1$-$C_6$ alkenyl, $C_1$-$C_6$ alkoxy, $C_1$-$C_6$ alkoxycarbonyl, —$(CH_2)_n$-amino, —$(CH_2)_n$-aryl, —$(CH_2)_n$-heteroaryl, —$(CH_2)_n$-heterocycle, or —$(CH_2)_n$-phenyl, wherein n is an integer from 0 to 10.

Other β-lapachone analogs and derivatives are disclosed in U.S. Pat. No. 5,763,625, U.S. Pat. No. 5,824,700, and U.S. Pat. No. 5,969,163, as well is in scientific journal articles, such as Sabba et al., *J Med Chem* 27:990-994 (1984), which discloses β-lapachone with substitutions at one or more of the following positions: 2-, 8- and/or 9-positions. See also Portela et al., *Biochem Pharm* 51:275-283 (1996) (substituents at the 2- and 9-positions); Maruyama et al., *Chem Lett* 847-850 (1977); Sun et al., *Tetrahedron Lett* 39:8221-8224 (1998); Goncalves et al., *Molecular and Biochemical Parasitology* 1:167-176 (1998) (substituents at the 2- and 3-positions); Gupta et al., *Indian Journal of Chemistry* 16B: 35-37 (1978); Gupta et al., *Curr Sci* 46:337 (1977) (substituents at the 3- and 4-positions); DiChenna et al., *J Med Chem* 44: 2486-2489 (2001) (monoarylamino derivatives).

More preferably, β-lapachone analogs and derivatives contemplated by the present application are intended to encompass compounds having the general formula I and II:

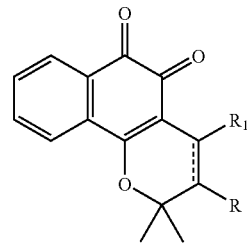

Formula I

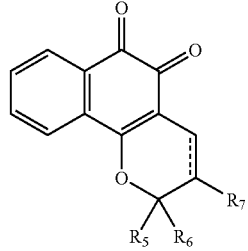

Formula II where the dotted double bond between the ring carbons represents an optional ring double bond and where R and $R_1$ are each independently selected from hydrogen, hydroxy, sulfhydryl, halogen, substituted alkyl, unsubstituted alkyl, substituted alkenyl, unsubstituted alkenyl, substituted aryl, unsubstituted aryl, substituted alkoxy, unsubstituted alkoxy, and salts thereof. The alkyl groups preferably have from 1 to about 15 carbon atoms, more preferably from 1 to about 10 carbon atoms, still more preferably from 1 to about 6 carbon atoms. The term alkyl refers to both cyclic and noncyclic groups. Straight or branched chain noncyclic alkyl groups are generally more preferred than cyclic groups. Straight chain alkyl groups are generally more preferred than branched. The alkenyl groups preferably have from 2 to about 15 carbon atoms, more preferably from 2 to about 10 carbon atoms, still more preferably from 2 to 6 carbon atoms. Especially preferred alkenyl groups have 3 carbon atoms (i.e., 1-propenyl or 2-propenyl), with the allyl moiety being particularly preferred. Phenyl and napthyl are generally preferred aryl groups. Alkoxy groups include those alkoxy groups having one or more oxygen linkage and preferably have from 1 to 15 carbon atoms, more preferably from 1 to about 6 carbon atoms. The substituted R and $R_1$ groups may be substituted at one or more available positions by one or more suitable groups such as, for example, alkyl groups having from 1 to 10 carbon atoms or from 1 to 6 carbon atoms, alkenyl groups having from 2 to 10 carbon atoms or 2 to 6 carbon atoms, aryl groups having from six to ten carbon atoms, halogen such as fluoro, chloro and bromo, and N, O and S, including heteroalkyl, e.g., heteroalkyl having one or more hetero atom linkages (and thus including alkoxy, aminoalkyl and thioalkyl) and from 1 to 10 carbon atoms or from 1 to 6 carbon atoms; and where $R_5$ and $R_6$ may be independently selected from hydroxy, $C_1$-$C_6$ alkyl, $C_1$-$C_6$ alkenyl, $C_1$-$C_6$ alkoxy, $C_1$-$C_6$ alkoxycarbonyl, —$(CH_2)_n$-aryl, —$(CH_2)_n$-heteroaryl, —$(CH_2)_n$-heterocycle, or —$(CH_2)_n$-phenyl; and $R_7$ is hydrogen, hydroxyl, $C_1$-$C_6$ alkyl, $C_1$-$C_6$ alkenyl, $C_1$-$C_6$ alkoxy, $C_1$-$C_6$ alkoxycarbonyl, —$(CH_2)_n$-amino, —$(CH_2)_n$-aryl, —$(CH_2)_n$-heteroaryl, —$(CH_2)_n$-heterocycle, or —$(CH_2)_n$-phenyl, wherein n is an integer from 0 to 10.

Preferred β-lapachone analogs and derivatives also contemplated by the invention include compounds of the following general formula III:

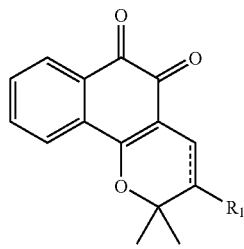

Formula III where $R_1$ is $(CH_2)_n$—$R_2$, where n is an integer from 0-10 and $R_2$ is hydrogen, an alkyl, an aryl, a heteroaromatic, a heterocyclic, an aliphatic, an alkoxy, an allyloxy, a hydroxyl, an amine, a thiol, an amide, or a halogen.

Analogs and derivatives also contemplated by the invention include 4-acetoxy-β-lapachone, 4-acetoxy-3-bromo-β-lapachone, 4-keto-β-lapachone, 7-hydroxy-β-lapachone, 7-methoxy-β-lapachone, 8-hydroxy-β-lapachone, 8-methoxy-β-lapachone, 8-chloro-β-lapachone, 9-chloro-β-lapachone, 8-methyl-β-lapachone and 8,9-dimethoxy-β-lapachone.

Other β-lapachone analogs and derivatives also contemplated by the invention include compounds of the following general formula IV:

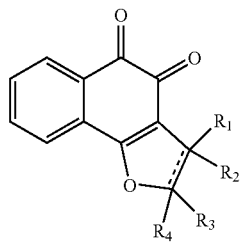

Formula IV where $R_1$-$R_4$ are each, independently, selected from the group consisting of H, $C_1$-$C_6$ alkyl, $C_1$-$C_6$ alkenyl, $C_1$-$C_6$ alkoxy, $C_1$-$C_6$ alkoxycarbonyl, —$(CH_2)_n$-aryl, —$(CH_2)_n$-heteroaryl, —$(CH_2)_n$-heterocycle, or —$(CH_2)_n$-phenyl; or $R_1$ and $R_2$ combined are a single substituent selected from the above group, and $R_3$ and $R_4$ combined are a single substituent selected from the above groups, in which case ---- is a double bond.

Preferred β-lapachone analogs and derivatives also contemplated by this invention include dunnione and 2-ethyl-6-hydroxynaphtho[2,3-b]-furan-4,5-dione.

Preferred β-lapachone analogs and derivatives also contemplated by the invention include compounds of the following general formula V:

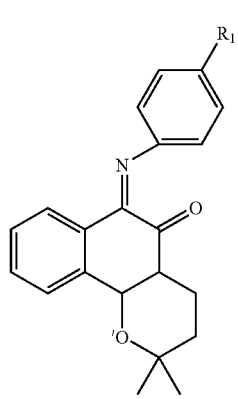

Formula V where $R_1$ is selected from H, $CH_3$, $OCH_3$ and $NO_2$.

Additional preferred β-lapachone analogs useful in the methods and kits of the invention are represented by Formula VI (see also the co-owned PCT patent application entitled "NOVEL LAPACHONE COMPOUNDS AND METHODS OF USE THEREOF", (WO 04/45557) filed Nov. 18, 2003, and claiming priority to U.S. provisional application No. 60/427,283, filed Nov. 18, 2002):

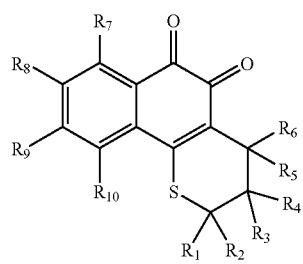

Formula VI or pharmaceutically acceptable salts thereof, or a regioisomeric mixture thereof, wherein R1-R6 are each, independently, selected from the group consisting of H, OH, substituted and unsubstituted $C_1$-$C_6$ alkyl, substituted and unsubstituted $C_1$-$C_6$ alkenyl, substituted and unsubstituted $C_1$-$C_6$ alkoxy, substituted and unsubstituted $C_1$-$C_6$ alkoxycarbonyl, substituted and unsubstituted $C_1$-$C_6$ acyl, —$(CH_2)_n$-amino, —$(CH_2)_n$-aryl, —$(CH_2)_n$-heterocycle, and —$(CH_2)_n$-phenyl; or one of R1 or R2 and one of R3 or R4; or one of R3 or R4 and one of R5 or R6 form a fused ring, wherein the ring has 4-8 ring members; R7-R10 are each, independently, hydrogen, hydroxyl, halogen, substituted or unsubstituted alkyl, substituted or unsubstituted alkoxy, nitro, cyano or amide; and n is an integer from 0 to 10.

In a preferred embodiment, R1 and R2 are alkyl, R3-R6 are, independently, H, OH, halogen, alkyl, alkoxy, substituted or unsubstituted acyl, substituted alkenyl or substituted alkyl carbonyl, and R7-R10 are hydrogen. In another preferred embodiment, R1 and R2 are each methyl and R3-R10 are each hydrogen. In another preferred embodiment, R1-R4 are each hydrogen, R5 and R6 are each methyl and R7-R10 are each hydrogen.

Additional preferred β-lapachone analogs useful in the methods and kits of the invention are represented by Formula VII (see also the co-owned PCT patent application entitled "NOVEL LAPACHONE COMPOUNDS AND METHODS OF USE THEREOF", filed Nov. 18, 2003):

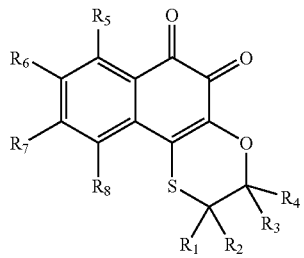

Formula VII or pharmaceutically acceptable salts thereof, or a regioisomeric mixture thereof, wherein R1-R4 are each, independently, selected from the group consisting of H, OH, substituted and unsubstituted $C_1$-$C_6$ alkyl, substituted and unsubstituted $C_1$-$C_6$ alkenyl, substituted and unsubstituted $C_1$-$C_6$ alkoxy, substituted and unsubstituted $C_1$-$C_6$ alkoxycarbonyl, substituted and unsubstituted $C_1$-$C_6$ acyl, —$(CH_2)_n$-amino, —$(CH_2)_n$-aryl, —$(CH_2)_n$-heterocycle, and —$(CH_2)_n$-phenyl; or one of R1 or R2 and one of R3 or R4 form a fused ring, wherein the ring has 4-8 ring members; R5-R8 are each, independently, hydrogen, hydroxyl, halogen, substituted or unsubstituted alkyl, substituted or unsubstituted alkoxy, nitro, cyano or amide; and n is an integer from 0 to 10. In certain embodiments of Formula VII, R1, R2, R3, R4, R5, R6, R7 and R8 are not each simultaneously H.

All stereoisomers of the compounds of the instant invention are contemplated, either in admixture or in pure or substantially pure form. The definition of the compounds according to the invention embraces all possible stereoisomers (e.g., the R and S configurations for each asymmetric center) and their mixtures. It very particularly embraces the racemic forms and the isolated optical isomers having a specified activity. The racemic forms can be resolved by physical methods, such as, for example, fractional crystallization, separation or crystallization of diastereomeric derivatives or separation by chiral column chromatography. The individual optical isomers can be obtained from the racemates by conventional methods, such as, for example, salt formation with an optically active acid followed by crystallization. Furthermore, all geometric isomers, such as E- and Z-configurations at a double bond, are within the scope of the invention unless otherwise stated. Certain compounds of this invention may exist in tautomeric forms. All such tautomeric forms of the compounds are considered to be within the scope of this invention unless otherwise stated. The present invention also includes one or more regioisomeric mixtures of an analog or derivative.

It will be appreciated that more than one modulator of cell cycle checkpoint activation can be administered to a subject, e.g., to decrease side effects, enhance efficacy, etc. In addition, other active agents, such as additional chemotherapeutic agents, can be combined with the modulator of cell cycle checkpoint activation to further treat the subject (e.g., combining chemotherapy with radiation therapy according to the invention). For examples of chemotherapeutic drugs that may be combined with modulators of cell cycle checkpoint activation such as β-lapachone, see, e.g., PCT Publication No. WO 00/61142.

As with the use of other chemotherapeutic drugs, the individual patient will be monitored in a manner deemed appropriate by the treating physician. Dosages can also be reduced if severe side effects, such as neutropenia or severe peripheral neuropathy occur, or if a grade 2 or higher level of mucositis is observed, using the Common Toxicity Criteria of the National Cancer Institute.

The agents described herein may be administered singly and sequentially, or in a cocktail or combination containing one or more of the agents with other therapeutic agents, including but not limited to, immunosuppressive agents, potentiators and side-effect relieving agents. The therapeutic agents will preferably be administered intravenously or otherwise systemically by injection intramuscularly, subcutaneously, intrathecally or intraperitoneally.

Pharmaceutical compositions useful in the methods and kits of this invention may exist in the dosage form as a solid, semi-solid, or liquid such as, e.g., suspensions, aerosols or the like. Preferably the compositions are administered in unit dosage forms suitable for single administration of precise dosage amounts. The compositions may also include, depending on the formulation desired, pharmaceutically-acceptable, nontoxic carriers or diluents, which are carriers commonly used to formulate pharmaceutical compositions for animal or human administration. The diluent is preferably selected so as not to adversely affect the biological activity of the combination. Examples of such diluents are distilled water, physiological saline, Ringer's solution, dextrose solution, and Hank's solution. A preferred carrier for the solubilization of β-lapachone is hydroxypropyl beta cyclodextrin, a water-solubilizing carrier molecule (see, e.g., U.S. Patent Publication 20030091639). Other water-solubilizing agents for combining with β-lapachone or other modulators of cell cycle checkpoint activation, such as Poloxamer, Povidone K17, Povidone K12, Tween 80, ethanol, Cremophor/ethanol, polyethylene glycol 400, propylene glycol and Trappsol, are contemplated. Furthermore, the invention is not limited to water-solubilizing agents, and oil-based solubilizing agents such as lipiodol and peanut oil, may also be used. Polymeric carriers can also be used to administer a modulator of cell cycle checkpoint activation such as β-lapachone (see, e.g., PCT Publication No. WO03090710). Biocompatible polymers carrying a modulator of cell cycle checkpoint activation may be provided in the form of microspheres, nanospheres, millirods, or other shapes or forms known to one of ordinary skill in the art.

In addition, the pharmaceutical composition or formulation may also include other carriers, adjuvants, or nontoxic, nontherapeutic, nonimmunogenic stabilizers and the like. Effective amounts of such diluent or carrier will be those amounts which are effective to obtain a pharmaceutically acceptable formulation in terms of solubility of components, or biological activity, and the like. Liposome formulations, are also contemplated by the present invention, and have been described (see, e.g. U.S. Pat. No. 5,424,073).

For the purposes of the present invention, modulators of cell cycle checkpoint activation described herein include their pharmacologically acceptable salts, preferably sodium; analogs containing halogen substitutions, preferably chlorine or fluorine; analogs containing ammonium or substituted ammonium salts, preferably secondary or tertiary ammonium salts; analogs containing alkyl, alkenyl, aryl or their alkyl, alkenyl, aryl, halo, alkoxy, alkenyloxy substituted derivatives, preferably methyl, methoxy, ethoxy, or phenylacetate; and natural analogs such as naphthyl acetate. Further, modulators of cell cycle checkpoint activation may be conjugated to a water-soluble polymer or may be derivatized with water-soluble chelating agents or radionuclides. Examples of water soluble polymers are, but not limited to: polyglutamic acid polymer, copolymers with polycaprolactone, polyglycolic acid, polyacetic acid, polyacrylic acid, poly(2-hydroxyethyl 1-glutamine), carboxymethyl dextran, hyaluronic acid, human serum albumin, polyalginic acid or a combination thereof. Examples of water-soluble chelating agents are, but not limited to: DIPA (diethylenetriaminepentaacetic acid), EDTA, DTTP, DOTA or their water-soluble salts, etc. Examples of radionuclides include, but not limited to: $^{111}$In, $^{90}$Y, $^{166}$Ho, $^{68}$Ga, $^{99m}$Tc, and the like.

Although oral administration is preferred in certain embodiments as discussed above, the invention is not intended to be limited in this respect, and the compounds can be administered by any means known in the art. Such modes include nasal, pulmonary, topical (including buccal and sublingual) or parenteral (including subcutaneous, intramuscular, intravenous and intradermal) administration.

For ease of administration and comfort to the patient, oral administration is generally preferred. However, oral administration typically requires the administration a higher dose than intravenous administration. Thus, depending upon the situation—the skilled artisan must determine which form of administration is best in a particular case—balancing dose needed versus the number of times (e.g., per day, per week, or per month) administration is necessary. Preferred oral dosage forms include tablets, capsules, wafers, dragees, syrups, suspensions, elixirs, lozenges, and the like.

In administering a modulator of cell cycle checkpoint activation (such as β-lapachone), the normal dose of such compound individually is utilized as set forth below. However, when combination therapies are used (e.g., more than one modulator of cell cycle checkpoint activation is administered to the patient) it is preferable to use a lower dosage of one or both of the modulators of cell cycle checkpoint activation than would be used if either modulator of cell cycle checkpoint activation was administered individually—typically 75% or less of the individual amount, more preferably 50% or less, still more preferably 40% or less.

In therapeutic applications, the dosages of the agents used in accordance with the invention vary depending on the agent, the age, weight, and clinical condition of the recipient patient, and the experience and judgment of the clinician or practitioner administering the therapy, among other factors affecting the selected dosage. Generally, the dose should be sufficient to result in prevention or treatment of radiation injury as described above.

The invention is further defined by reference to the following Examples. It is understood that the foregoing detailed description and the following example are illustrative only and are not to be taken as limitations upon the scope of the invention. It will be apparent to those skilled in the art that many modifications, both to the materials and methods, may be practiced without departing from the purpose and interest of the invention.

EXAMPLES

Example 1

Figure 2:
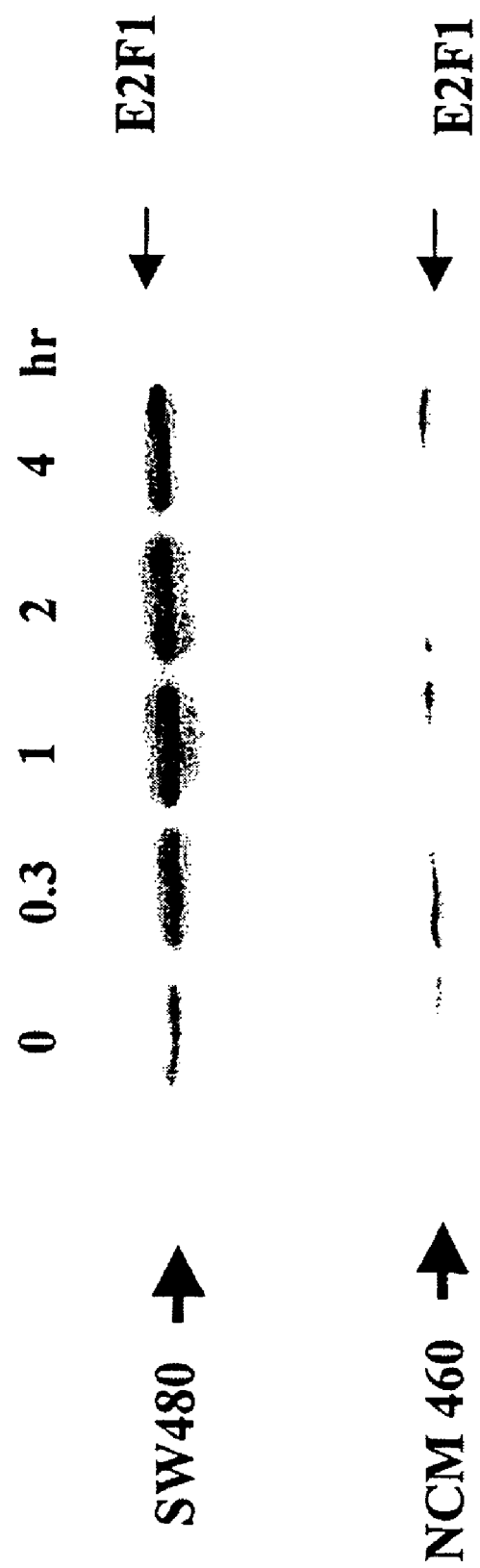
FIG. 2 illustrates that β-lapachone induces increased expression of E2F1 in human colon cancer cells, but not in similarly treated normal human colon cells.

Human colon cancer cells (SW480) and normal colon cells (NCM460) are treated with β-lapachone at a concentration of 2 μM and are harvested after 20 minute, 1 hour, 2 hour, or 4 hour exposures. Whole cell extracts are prepared and resolved by SDS/PAGE. An enhanced chemiluminescence assay system (Amersham Pharmacia) is used to determine the E2F1 level. Monoclonal antibody against E2 μl is obtained from Santa Cruz Biotechnology (Santa Cruz, Calif.). Elevation of E2F1 is seen in tumor cells, but not normal cells, as soon as 20 minutes following exposure to β-lapachone (FIG. 2). Elevation of E2F1 following exposure to β-lapachone persists through cell death in cancer cells.

Example 2

Figure 3:
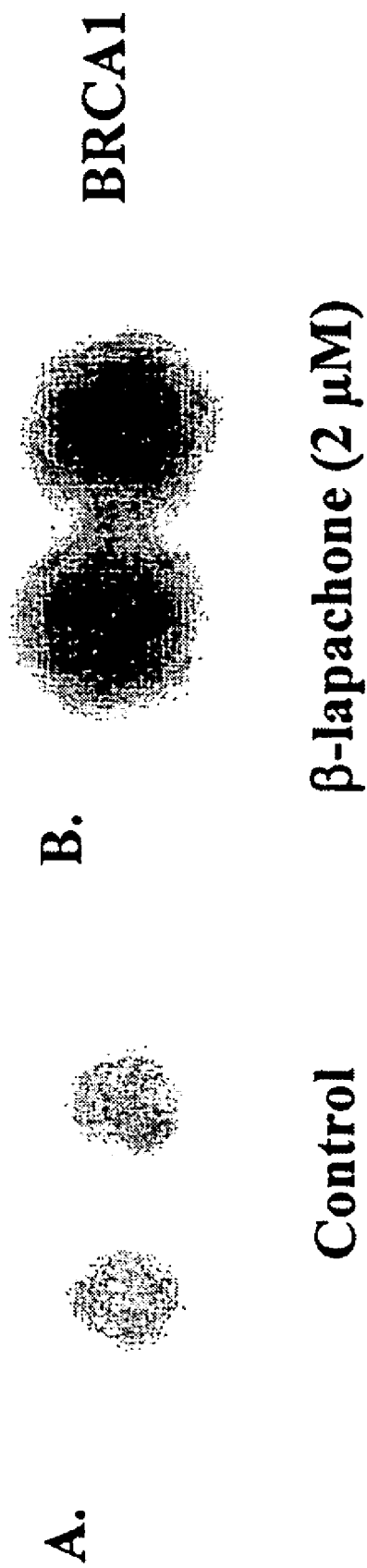
FIG. 3 illustrates that β-lapachone induces increased expression in human colon cancer cells of BRCA1.

Exponentially growing human colon cancer cells (SW480) are treated with β-lapachone at 2 μM, or carrier alone control, for 4 hours. Total RNA is prepared by Trizol reagents. Relative expression levels of multiple genes involved in cell cycle checkpoint are determined with the Human Cell-cycle Checkpoint GEArray Kit (SuperArray Inc. Bethesda, Md.) (FIG. 3). The up-regulation of the E2F1 target BRCA1 in β-lapachone treated cancer cells is another indication of E2F1 activation. BRCA1 is a tumor suppressor involved in many roles within the cell including DNA repair.

Example 3

Figure 4:
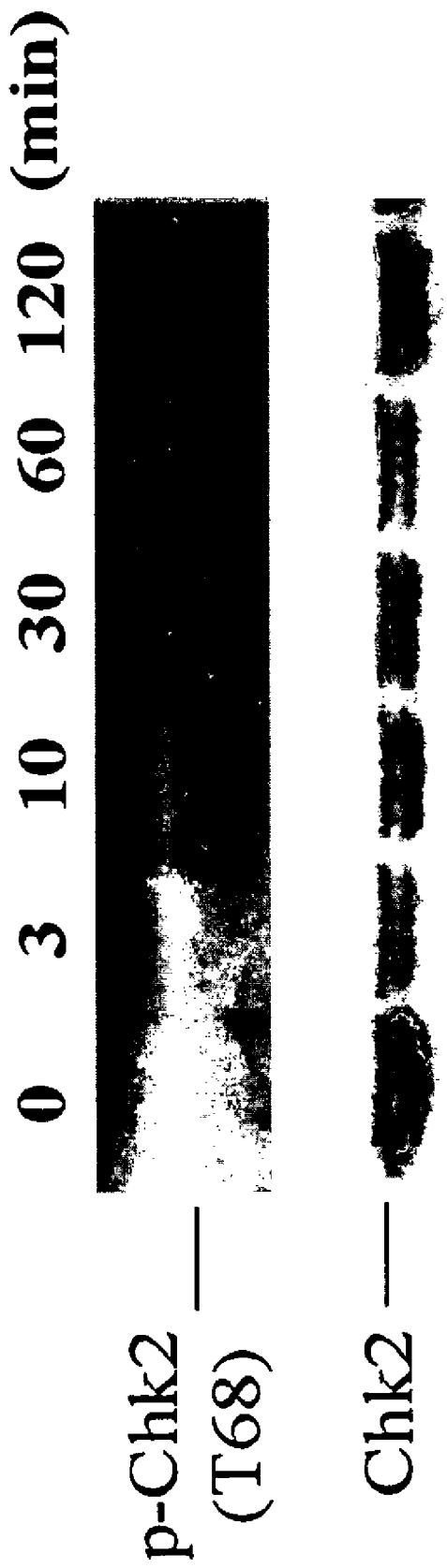
FIG. 4 illustrates that β-lapachone induces an increase in the proportion of phosphorylated Chk2 in HeLa cells.

Human cervical cancer cells (HeLa) are treated with 4 μM β-lapachone for 0, 3, 10, 30, 60 and 120 minutes. Whole cell lysates are prepared, separated by SDS-PAGE, and analyzed by immunoblotting with anti-Chk2 and anti-phosphorylated-Chk2 antibodies. Phosphorylated Chk2 (p-Chk2) levels appear as soon as 10 minutes and continue to increase up to 120 minutes. β-lapachone induces a sustained increase in the active phosphorylated form of Chk2, via phosphorylation of the target residue threonine 68 (T68). While the phosphorylated form of Chk2 increased after treatment with β-lapachone, the total amount of Chk2 within the cells remains unchanged throughout the time course (FIG. 4). As such, the proportion of phosphorylated Chk2 is elevated after treatment with β-lapachone (i.e., after β-lapachone treatment, the fraction of phosphorylated Chk2 is increased relative to the total amount of Chk2 within the cells, which does not change following β-lapachone treatment).

Example 4

Methods and Design

Drug Formulations:

β-lapachone is prepared at 10 mg/ml in 40% hydroxypropyl-beta-cyclodextrin (HPBCD).

Animals

C57BL/6J inbred strain female mice (4-5 weeks old) are used. Animals are maintained in a climate-controlled animal facility.

Drug Treatment

Animals are injected with different concentrations of β-lapachone (20 and 40 mg/kg body weight) intraperitoneally 4 hours before or after irradiation.

Irradiation

Whole body irradiation of animals with 8 Gy of γ-rays is carried out in air at room temperature in a gamma chamber (Gammacell 40 Exactor), at a dose-rate of 1.05 Gy/min. This radiation dose is within the range of equivalent human exposures predicted in many scenarios of radiologic or nuclear terrorist attack.

Survival of Animals

Mice are divided into the following groups (each Group comprises four mice receiving identical treatment):

Group I: Mice receive radiation only and serve as control.

Group II: Mice are injected with β-lapachone 20 mg/kg body weight 4 hours before radiation.

Group III: Mice are injected with β-lapachone 40 mg/kg body weight 4 hours before radiation.

Group IV: Mice are injected with β-lapachone 20 mg/kg body weight 4 hours after radiation.

Group V: Mice are injected with β-lapachone 40 mg/kg body weight 4 hours after radiation.

Group VI: Mice are injected with amifostine 10 mg/kg body weight 4 hours before radiation.

Radiation Exposure and Death Profile

Animals are irradiated with 8 Gy at 1.05 Gy/min dose-rate. After irradiation mice are returned to their cage and observed on a regular basis. The radiation induced death profile and its modulation by β-lapachone is shown in Table 1. Exposure to γ-rays causes lethality in animals. Importantly, treatment with β-lapachone, especially at a level of 40 mg/kg prior to irradiation, diminishes the death rate.

Effect of β-Lapachone on Survival Time

Effect of irradiation on median survival time and modulation by β-lapachone is shown in Table 2. In the group of animals which were injected with β-lapachone (40 mg/kg) 4 hours before the irradiation (8 Gy), the median survival time was found to be enhanced from 16.4 days to 25 days (compared to the irradiation-only control group). In contrast, treatment with amifostine (a known radioprotectant) at 10 mg/kg showed little or no effect on median survival times.

Temporal Survival Pattern

Figure 5:
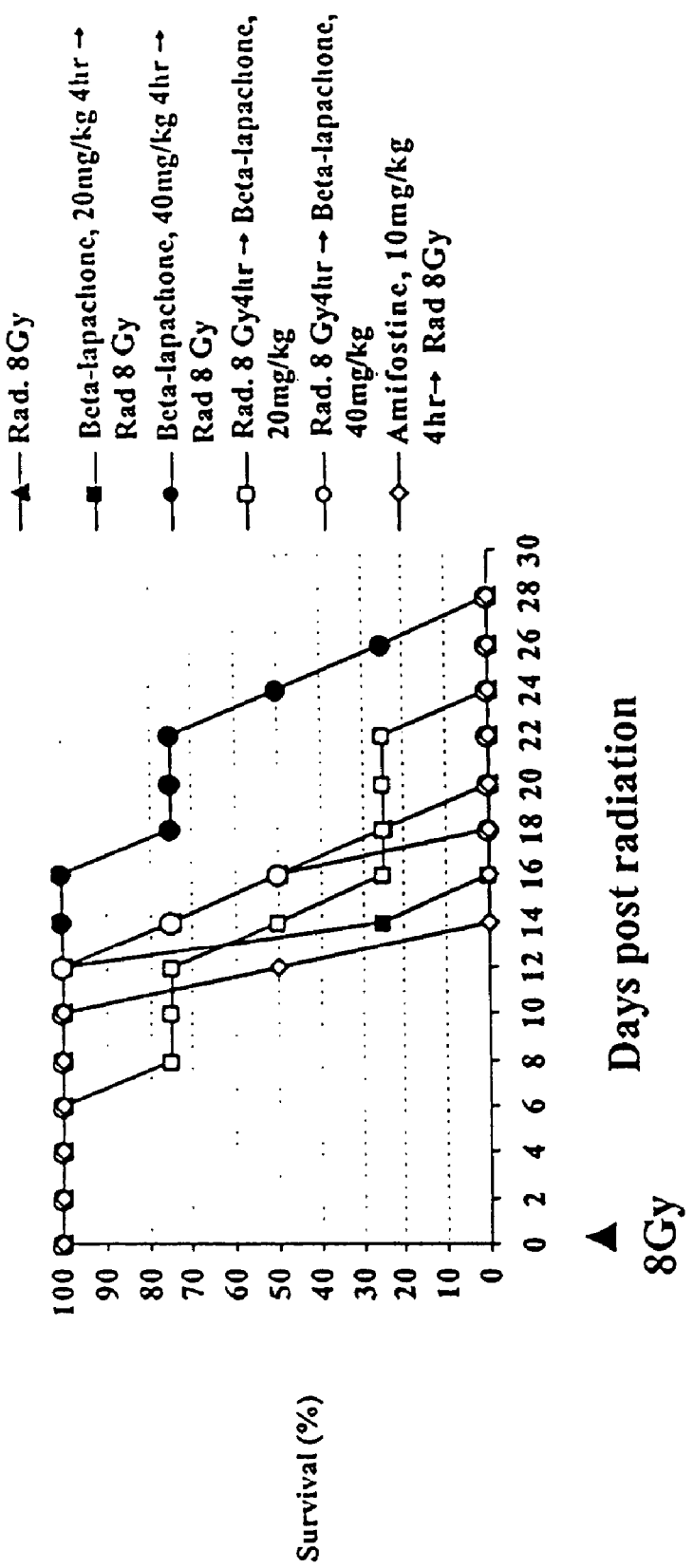
FIG. 5 illustrates survival rates of mice treated with varying concentrations of β-lapachone, administered intraperitoneally either 4 hours before or after whole-body irradiation with 8 Gy gamma rays, compared to survival rates of mice receiving irradiation only.

FIG. 5 depicts the temporal survival pattern of mice irradiated with 8 Gy with pretreatment or after treatment with β-lapachone (20, 40 mg/kg body weight). A sharp decline in survival was seen in the control group between 10-14 days. Administration of β-lapachone delayed this early decline in survival (especially at 40 mg/kg dosed prior to irradiation, although the death rate at 20 days was also decreased in the group treated with 20 mg/kg β-lapachone 4 hours post-radiation).

TABLE 1

Effect of γ-rays on the death profile of C57Bl/6J female mice and radioprotective efficacy of β-lapachone.

| Treatment | No. of animals (initial) | No. of animals surviving at 20 days post-irradiation | Death rate (%) |
|---|---|---|---|
| Radiation 8 Gy | 4 | 0 | 100 |
| β-lapachone, 20 mg/kg 4 hr → Radiation 8 Gy | 4 | 0 | 100 |
| β-lapachone, 40 mg/kg 4 hr → Radiation 8 Gy | 4 | 3 | 25 |
| Radiation 8 Gy 4 hr → β-lapachone, 20 mg/kg | 4 | 1 | 75 |
| Radiation 8 Gy 4 hr → β-lapachone, 20 mg/kg | 4 | 0 | 100 |
| Amifostine, 10 mg/kg 4 hr → Radiation 8 Gy | 4 | 0 | 100 |

TABLE 2

Effect of γ-rays on the median survival time and its modulation by β-lapachone in C57Bl/6J female mice.

| Treatment | Median survival time in days |
|---|---|
| Radiation 8 Gy | 16.4 |
| β-lapachone, 20 mg/kg 4 hr → Radiation 8 Gy | 13.5 |
| β-lapachone, 40 mg/kg 4 hr → Radiation 8 Gy | 25 |
| Radiation 8 Gy 4 hr → β-lapachone, 20 mg/kg | 14 |
| Radiation 8 Gy 4 hr → β-lapachone, 40 mg/kg | 16.4 |
| Amifostine, 10 mg/kg 4 hr → Radiation 8 Gy | 12 |

Example 5

Methods and Design

Drug Formulations:

β-lapachone is prepared at 10 mg/ml in 40% hydroxypropyl-beta-cyclodextrin (HPBCD).

Animals

C57BL/6J inbred strain female mice (4-5 weeks old) are used. Animals are maintained in a climate-controlled animal facility.

Drug Treatment

The animals are injected intraperitoneally with β-lapachone (40 mg/kg body weight) either 0.5 hour, 1 hour, or 4 hours before irradiation, or 10 minutes or 1 hour after irradiation.

Irradiation

Whole body irradiation of animals with 8 Gy of γ-rays is carried out in air at room temperature in a gamma chamber (Gammacell 40 Exactor) with a dose-rate of 1.05 Gy/min. This radiation dose is within the range of equivalent human exposures predicted in many scenarios of radiologic or nuclear terrorist attack.

Survival of Animals

Mice are divided in following groups (each Group comprises eight mice receiving identical treatment):

Group I: Control (mice receive no radiation).

Group II: Mice are injected with 40% HPBCD 4 ml/kg body weight 1 hour before radiation.

Group III: Mice are injected with β-lapachone 40 mg/kg body weight 4 hours before radiation.

Group IV: Mice are injected with β-lapachone 40 mg/kg body weight 1 hour before radiation.

Group V: Mice are injected with β-lapachone 40 mg/kg body weight 0.5 hours before radiation.

Group VI: Mice are injected with β-lapachone 40 mg/kg body weight 10 minutes after radiation.

Group VII: Mice are injected with β-lapachone 40 mg/kg body weight 1 hour after radiation.

Radiation Exposure and Death Profile

Animals are irradiated with 8 Gy at 1.05 Gy/min dose-rate. After irradiation mice are returned to their cage and observed on a regular basis. The radiation induced death profile and its modulation by β-lapachone is shown in Table 3. Exposure to γ-rays causes lethality in animals. Importantly, treatment with β-lapachone, especially at a level of 40 mg/kg either 4, 1, or 0.5 hours prior to irradiation, diminishes the death rate.

Effect of β-Lapachone on Survival Time

Effect of irradiation on median survival time and modulation by β-lapachone is shown in Table 4. In the group of animals which were injected with β-lapachone (40 mg/kg) 4 hours before the irradiation (8 Gy), the median survival time was found to be enhanced from 16.4 days to 21 days (compared to the irradiation-only control group). In the group of animals which were injected with β-lapachone (40 mg/kg) 1 hour before the irradiation (8 Gy), the median survival time was found to be enhanced from 16.4 days to 68 days (compared to the irradiation-only control group). In the group of animals which were injected with β-lapachone (40 mg/kg) 0.5 hours before the irradiation (8 Gy), the median survival time was found to be enhanced from 16.4 days to >68 days (no death) (compared to the irradiation-only control group).

Temporal Survival Pattern

Figure 6:
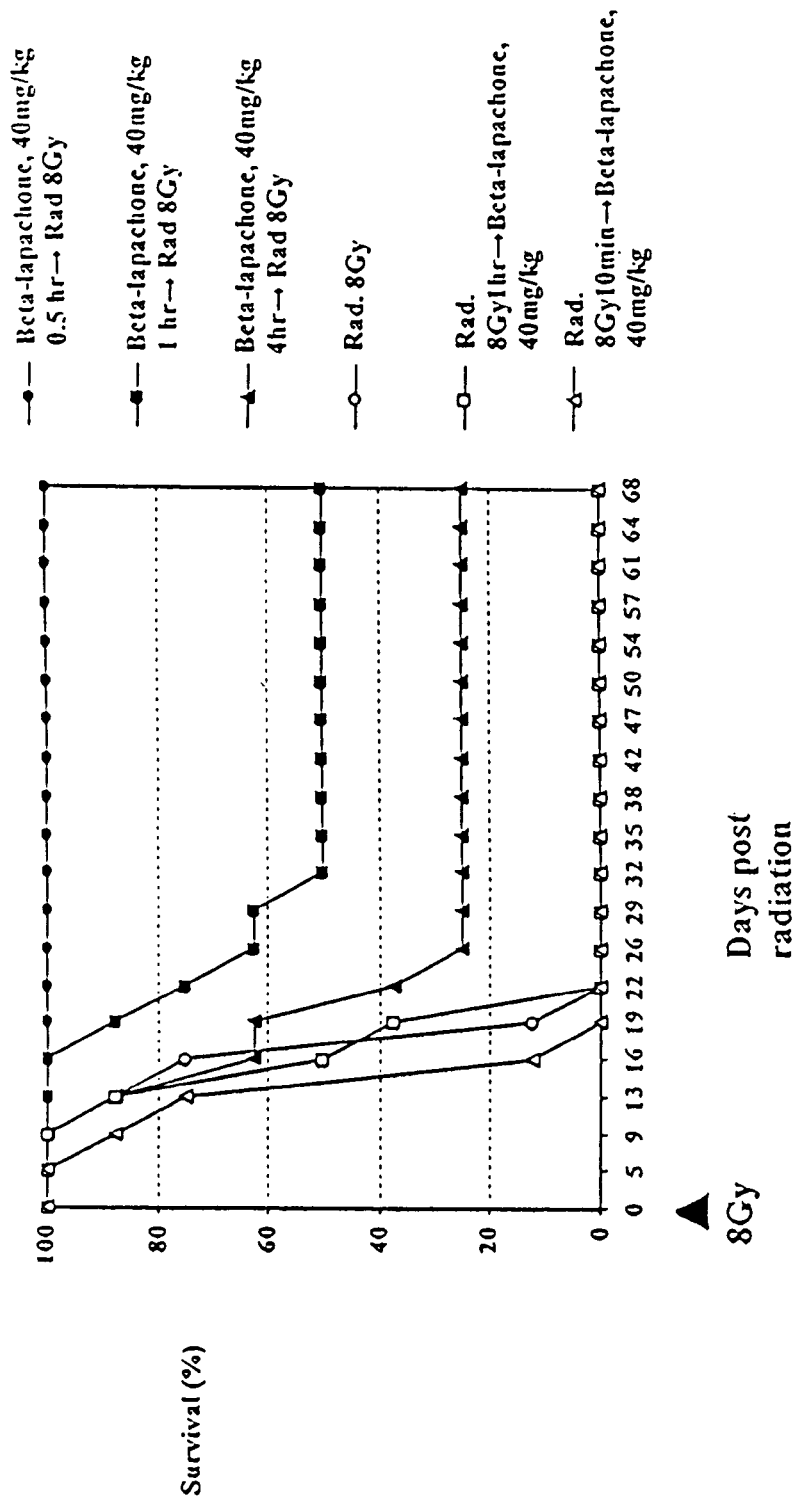
FIG. 6 illustrates survival rates of mice treated with constant concentrations of β-lapachone or vehicle control (40% HPBCD), administered intraperitoneally at varying time points either before or after whole-body irradiation with 8 Gy gamma rays, compared to survival rates of mice receiving irradiation only.

FIG. 6 depicts the temporal survival pattern of mice irradiated with 8 Gy with pretreatment or after treatment with β-lapachone (40 mg/kg body weight). A sharp decline in survival was seen in the control group between 16-20 days. Administration of β-lapachone at 0.5, 1.0 or four hours prior to irradiation delayed this early decline in survival.

TABLE 3

Effect of γ-rays on the death profile of C57Bl/6J female mice and radioprotective efficacy of β-lapachone.

| Treatment | No. of animals (initial) | No. of animals surviving at 68 days post-irradiation | Death rate (%) |
| --- | --- | --- | --- |
| 0 (No Radiation) | 8 | 8 | 0 |
| Radiation 8 Gy | 8 | 0 | 100 |
| β-lapachone, 40 mg/kg 4 hr → Radiation 8 Gy | 8 | 2 | 75 |
| β-lapachone, 40 mg/kg 1 hr → Radiation 8 Gy | 8 | 4 | 50 |
| β-lapachone, 40 mg/kg 0.5 hr → Radiation 8 Gy | 8 | 8 | 0 |
| Radiation 8 Gy 10 min → β-lapachone, 40 mg/kg | 8 | 0 | 100 |
| Radiation 8 Gy 1 hr → β-lapachone, 40 mg/kg | 8 | 0 | 100 |

TABLE 4

Effect of γ-rays on the median survival time and its modulation by β-lapachone in C57Bl/6J female mice.

| Treatment | Median survival time in days |
| --- | --- |
| 0 (No Radiation) | >68 (no death) |
| Radiation 8 Gy | 16.4 |
| β-lapachone, 40 mg/kg 4 hr → Radiation 8 Gy | 21 |
| β-lapachone, 40 mg/kg 1 hr → Radiation 8 Gy | 68 |
| β-lapachone, 40 mg/kg 0.5 hr → Radiation 8 Gy | >68 (no death) |
| Radiation 8 Gy 10 min → β-lapachone, 40 mg/kg | 14 |
| Radiation 8 Gy 1 hr → β-lapachone, 40 mg/kg | 16 |

This experiment shows that administration of β-lapachone, especially prior to exposure to radiation, can significantly delay lethality and at certain doses can provide complete protection against radiation induced lethality (e.g., Tables 2 and 4). β-lapachone can delay the early decline in survival that is observed in irradiated subjects, suggesting the β-lapachone has radioprotective properties.

Example 6

Methods and Design

Drug Formulations:

β-lapachone is prepared at 10 mg/ml in 40% hydroxypropyl-beta-cyclodextrin (HPBCD).

Animals

C57BL/6J inbred strain female mice (4-5 weeks old) are used. Animals are maintained in a climate-controlled animal facility.

Drug Treatment

β-lapachone (200 mg/kg body weight) is orally administered to animals at either 0.5 hour, 1 hour, 2 hours, 4 hours or 6 hours before irradiation.

Irradiation

Whole body irradiation of animals with 8 Gy of γ-rays is carried out in air at room temperature in a gamma chamber (Gammacell 40 Exactor), at a dose-rate of 1.05 Gy/min. This radiation dose is within the range of equivalent human exposures predicted in many scenarios of radiologic or nuclear terrorist attack.

Survival of Animals

Mice are divided in following groups (each Group comprises 8 mice receiving identical treatment):

Group I: Mice receive no radiation, no β-lapachone, and no carrier.

Group II: Carrier (40% HPBCD 4 ml/kg body weight) is orally administered to mice 1 hour before radiation.

Group III: β-lapachone (200 mg/kg body weight) is orally administered to mice 6 hours before radiation.

Group IV: β-lapachone (200 mg/kg body weight) is orally administered to mice 4 hours before radiation.

Group V: β-lapachone (200 mg/kg body weight) is orally administered to mice 2 hours before radiation.

Group VI: β-lapachone (200 mg/kg body weight) is orally administered to mice 1 hour before radiation.

Group VII: β-lapachone (200 mg/kg body weight) is orally administered to mice 0.5 hour before radiation.

Radiation Exposure and Death Profile

Animals are irradiated with 8 Gy at 1.05 Gy/min dose-rate. After irradiation mice are returned to their cage and observed on a regular basis. The radiation induced death profile and its modulation by β-lapachone is shown in Table 5. Exposure to γ-rays causes lethality in animals. Importantly, treatment with β-lapachone, especially at a level of 200 mg/kg orally at one hour prior to irradiation, diminishes the death rate.

TABLE 5

Effect of γ-rays on the death profile of C57Bl/6J female mice and radioprotective efficacy of β-lapachone.

| Treatment | No. of animals (initial) | No. of animals surviving at 20 days post-irradiation | Death rate (%) |
|---|---|---|---|
| Radiation 8 Gy | 10 | 0 | 100 |
| β-lapachone, 200 mg/kg p.o. 6 hr → Radiation 8 Gy | 10 | 1 | 90 |
| β-lapachone, 200 mg/kg p.o. 4 hr → Radiation 8 Gy | 10 | 0 | 100 |
| β-lapachone, 200 mg/kg p.o. 2 hr → Radiation 8 Gy | 10 | 0 | 100 |
| β-lapachone, 200 mg/kg p.o. 1 hr → Radiation 8 Gy | 10 | 3 | 70 |
| β-lapachone, 200 mg/kg p.o. 0.5 hr → Radiation 8 Gy | 10 | 0 | 100 |

TABLE 6

Effect of γ-rays on the median survival time and its modulation by β-lapachone in C57Bl/6J female mice.

| Treatment | Median survival time in days |
|---|---|
| Radiation 8 Gy | 13 |
| β-lapachone, 200 mg/kg p.o. 6 hr → Radiation 8 Gy | 18 |
| β-lapachone, 200 mg/kg p.o. 4 hr → Radiation 8 Gy | 14 |
| β-lapachone, 200 mg/kg p.o. 2 hr → Radiation 8 Gy | 10 |
| β-lapachone, 200 mg/kg p.o. 1 hr → Radiation 8 Gy | 18 |
| β-lapachone, 200 mg/kg p.o. 0.5 hr → Radiation 8 Gy | 10 |

Effect of β-Lapachone on Survival Time

Effect of irradiation on median survival time and modulation by β-lapachone is shown in Table 6. In the group of animals which receive oral administration of β-lapachone (200 mg/kg) 1 hour before the irradiation (8 Gy), the median survival time was found to be enhanced from 13 days to 18 days (compared to the irradiation-only control group).

Temporal Survival Pattern

Figure 7:
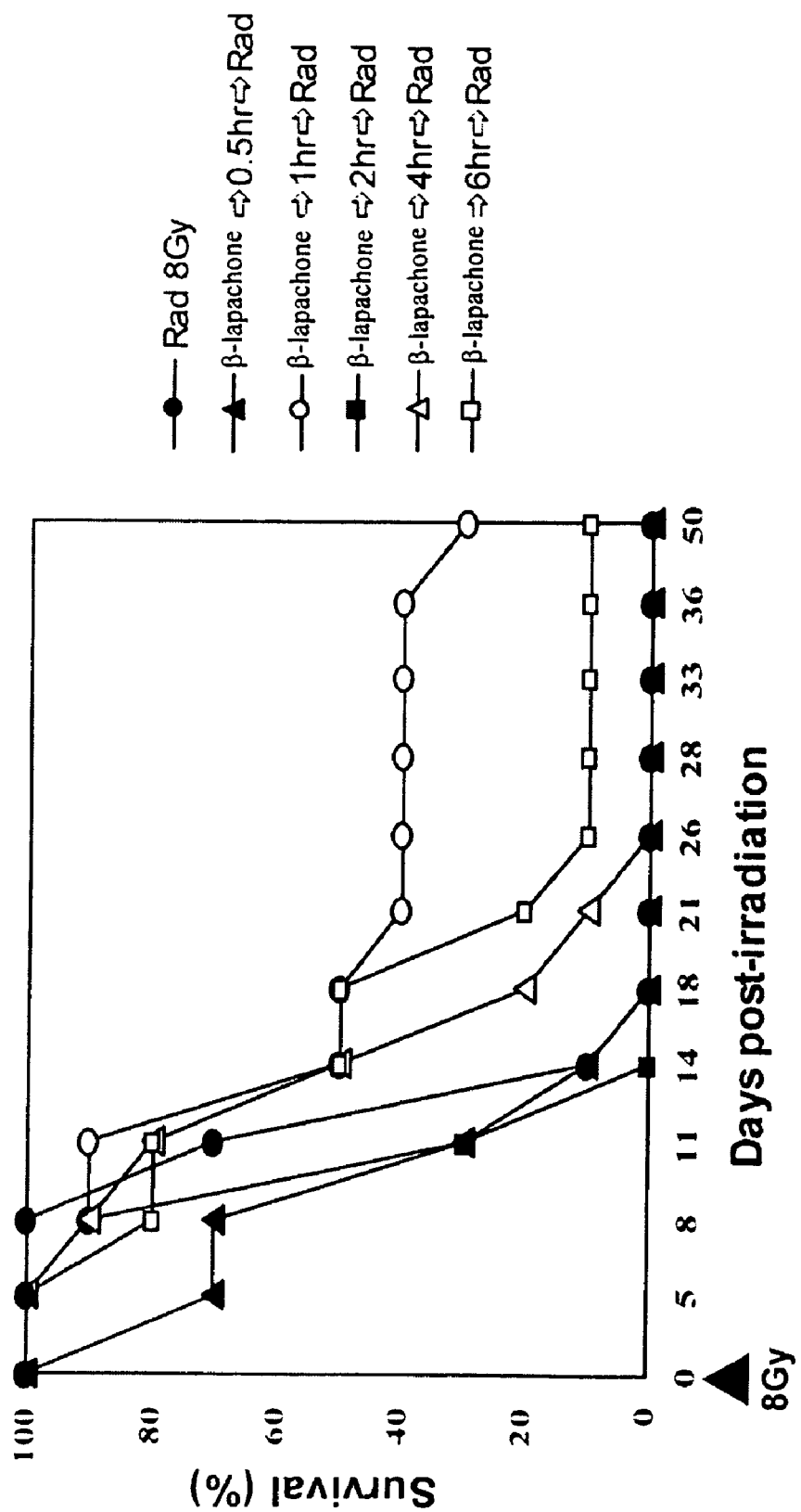
FIG. 7 illustrates survival rates of mice treated with constant concentrations of β-lapachone or vehicle control (40% HPBCD), administered orally at varying time points before whole-body irradiation with 8 Gy gamma rays, compared to survival rates of mice receiving irradiation only.

FIG. 7 depicts the temporal survival pattern of mice irradiated with 8 Gy with oral pretreatment with β-lapachone (200 mg/kg body weight). A sharp decline in survival was seen in the control group between 16-20 days. Oral administration of β-lapachone (200 mg/kg body weight) at 1 hour prior to irradiation led to the survival of more than 30% of the treated mice at day 50 post irradiation.

Example 7

Example 7a

It has been recently demonstrated that thymus output of mature T cells can be readily measured, not only early in life, but also in adults long after adolescence. See, e.g., Douek D C, McFarland R D, Keiser P H, et al., Nature (1998) 396:690-669. Thymic cellularity is assessed following whole body gamma irradiation in mice, with and without β-lapachone treatment, as follows.

β-lapachone is prepared at 10 mg/ml in 40% hydroxypropyl-beta-cyclodextrin (HPBCD). C57BL/6J inbred strain female mice (4-5 weeks old) are organized into three groups of six mice each: Group I mice receive no radiation, no β-lapachone, and no carrier; Group II mice receive radiation and are injected with carrier (40% HPBCD 4 ml/kg body weight); and Group III mice are injected intraperitoneally at 0.5 hour before irradiation with β-lapachone (40 mg/kg body weight). Whole body irradiation of animals with 8 Gy of γ-rays is carried out in air at room temperature in a gamma chamber (Gammacell 40 Exactor), with a dose-rate of 1.05 Gy/min. This radiation dose is within the range of equivalent human exposures predicted in many scenarios of radiologic or nuclear terrorist attack. Following irradiation, animals are maintained in a climate-controlled animal facility. Three mice in each of Groups I, II, and III are sacrificed on day five following irradiation, and an analysis of thymic cellularity is performed for each. The remaining mice are sacrificed on day eight following irradiation, and an analysis of thymic cellularity is performed for each. Thymic cellularity is qualitatively assessed in sections stained with hematoxylin-eosin following standard procedures.

Figure 8:
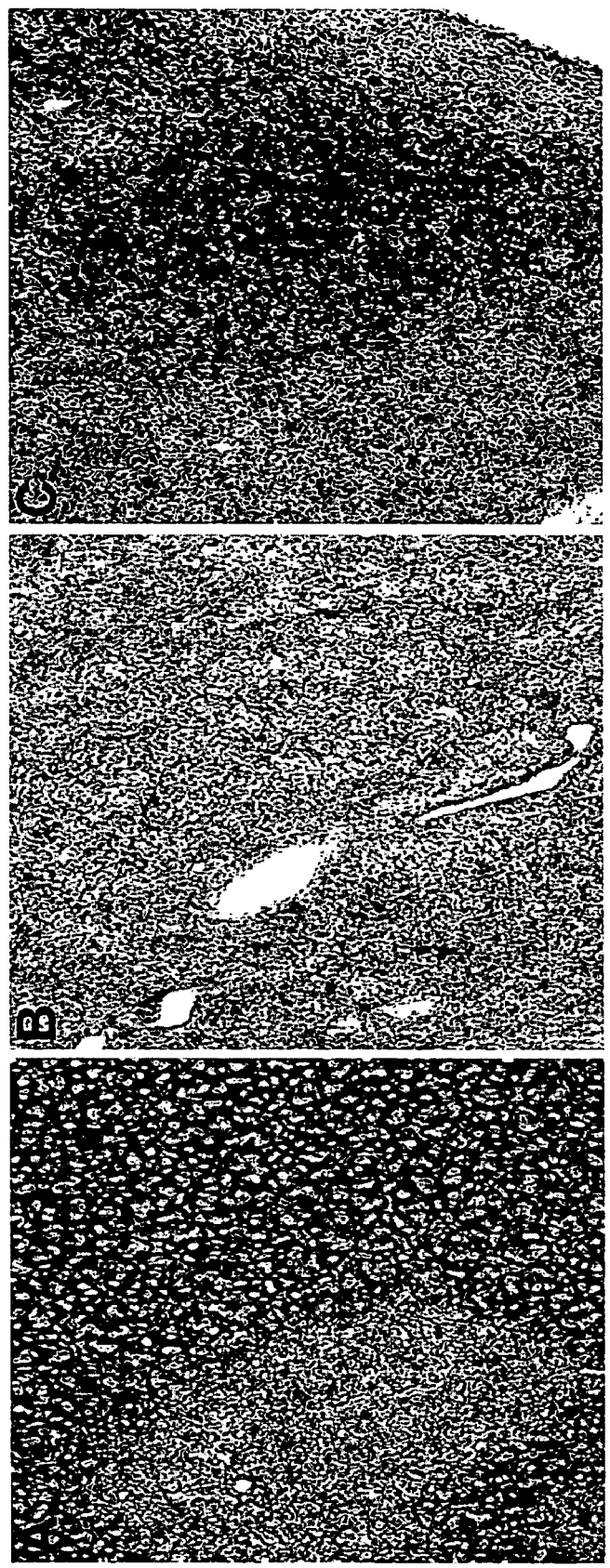
FIG. 8 illustrates thymic cellularity in mice treated with β-lapachone or vehicle control (40% HPBCD), administered intraperitoneally before irradiation with 8 Gy gamma rays, compared to thymic cellularity in mice receiving irradiation only.

In the absence of treatment with β-lapachone, thymic cellularity is observed to be substantially disrupted in thymic sections taken on day five following 8 Gy whole body irradiation of mice, as shown in FIG. 8, panel C. Pretreatment of mice with β-lapachone preserves thymic cellularity in thymic sections taken on day five following 8 Gy whole body irradiation, as shown in FIG. 8, panel B. FIG. 8, panel A sets forth normal mouse thymus in a non-irradiated control animal.

Example 7b

Spleen cellularity is quantitatively assessed following whole body gamma irradiation in mice, with and without pretreatment with β-lapachone, as follows. β-lapachone is prepared at 10 mg/ml in 40% hydroxypropyl-beta-cyclodextrin (HPBCD). C57BL/6J inbred strain female mice (4-5 weeks old) are organized into three groups of six mice each: Group I mice receive no radiation, no β-lapachone, and no carrier; Group II mice receive radiation and are injected with carrier (40% HPBCD 4 ml/kg body weight); and Group III mice are injected intraperitoneally at 0.5 hour before irradiation with β-lapachone (40 mg/kg body weight). Whole body irradiation of animals with 8 Gy of γ-rays is carried out in air at room temperature in a gamma chamber (Gammacell 40 Exactor), with a dose-rate of 1.05 Gy/min. This radiation dose is within the range of equivalent human exposures predicted in many scenarios of radiologic or nuclear terrorist attack. Following irradiation, animals are maintained in a climate-controlled animal facility. Three mice in each of Groups I, II, and III are sacrificed on day five following irradiation, and a quantitative analysis of splenic cellularity is performed for each. The remaining mice are sacrificed on day eight following irradiation, and a quantitative analysis of splenic cellularity is performed for each.

Figure 9:
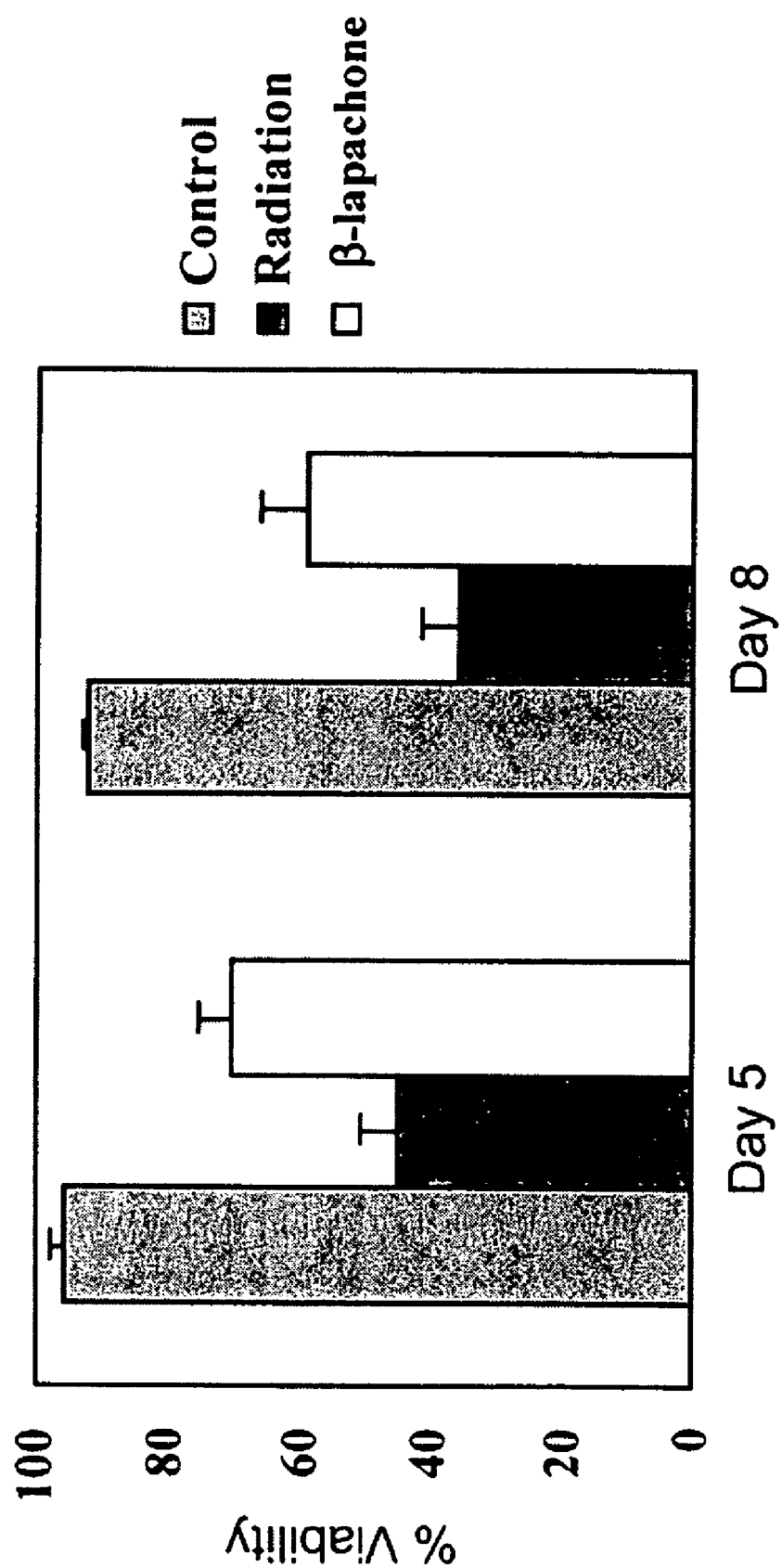
FIG. 9 illustrates spleen cellularity in mice treated with β-lapachone or vehicle control (40% HPBCD), administered intraperitoneally before irradiation with 8 Gy gamma rays, compared, quantitatively, to spleen cellularity in mice receiving irradiation only.

For quantitative analysis for splenic cellularity, spleens are processed into single cell suspensions and erythrocytes are lysed in 2 ml lysis buffer (0.01 M KHCO$_3$, 0.154 M NH$_4$Cl, 0.01 mM EDTA). The remaining leukocytes are washed, suspended and counted in a hemacytometer using the trypan blue exclusion method. In the absence of treatment with α-lapachone (i.e., carrier alone), splenic cellularity is observed to be substantially disrupted in splenic sections taken on day five and eight following whole body irradiation of mice, as shown in FIG. 9. β-lapachone pretreatment significantly preserved cellularity in splenic sections taken on day five and eight following whole body irradiation of mice, as shown in FIG. 9 (P=0.00035).

Example 7c

Spleen cellularity is also assessed by histologic analysis of stained spleen following whole body gamma irradiation in mice, with and without pretreatment with β-lapachone, as follows.

Figure 10:
FIG. 10 illustrates spleen cellularity in mice treated with β-lapachone or vehicle control (40% HPBCD), administered intraperitoneally before irradiation with 8 Gy gamma rays, compared, histologically, to spleen cellularity in mice receiving irradiation only.

Spleen cellularity is qualitatively assessed following whole body gamma irradiation in mice, with and without pretreatment with β-lapachone, as follows. β-lapachone is prepared at 10 mg/ml in 40% hydroxypropyl-beta-cyclodextrin (HP-BCD). C57BL/6J inbred strain female mice (4-5 weeks old) are organized into three groups of six mice each: Group I mice receive no radiation, no β-lapachone, and no carrier; Group II mice receive radiation and are injected with carrier (40% HPBCD 4 ml/kg body weight); and Group III mice are injected intraperitoneally at 0.5 hour before irradiation with β-lapachone (40 mg/kg body weight). Whole body irradiation of animals with 8 Gy (lethal radiation) or 5 Gy (sublethal radiation) of γ-rays is carried out in air at room temperature in a gamma chamber (Gammacell 40 Exactor), with a dose-rate of 1.05 Gy/min. This radiation dose is within the range of equivalent human exposures predicted in many scenarios of radiologic or nuclear terrorist attack. Following irradiation, animals are maintained in a climate-controlled animal facility. Three mice in each of Groups I, II, and III are sacrificed on day five following irradiation, and an analysis of splenic cellularity is performed for each. The remaining mice are sacrificed on day eight following irradiation, and an analysis of splenic cellularity is performed for each. Splenic cellularity is qualitatively assessed in sections stained with hematoxylin-eosin following standard procedures.

β-lapachone had a protective effect on spleen structure and cellularity as judged histologically five days after whole body irradiation of mice with the nonlethal dose of 5 Gy. Under these conditions, the spleen of irradiated mice receiving no β-lapachone was severely disrupted with few lymphocytes remaining (FIG. 10, panel C), while the spleens of mice receiving β-lapachone treatment and irradiation were still well structured, with lymphocytes largely preserved in the germinal center of the spleen (FIG. 10, panel B). FIG. 10, panel A sets forth normal unirradiated mouse spleen: under the capsule there are a few clear germinal centers and clear sinus.

The radiation dose and time to death in irradiated mice untreated with β-lapachone is consistent with morbidity associated with immune dysfunction secondary to the hematopoietic syndrome (see, e.g., Examples 4-6). β-lapachone appears to have a profound impact in protecting the normal cellularity of thymus and spleen from radiation-induced damage (see, e.g., Example 7). β-lapachone also appears to have a profound impact in protecting the normal histology of thymus and spleen, and protecting the normal structure of thymus and spleen from radiation-induced damage (see, e.g., Example 7). It is believed that the ability of β-lapachone to preserve the architectural structure and cellularity of secondary lymphoid organs (e.g., thymus and spleen) following irradiation plays an important role in the ability of β-lapachone to protect mice from lethal doses of irradiation.

Example 8

The effect of β-lapachone pre-treatment on radiation-induced leukopenia (e.g., radiation-induced neutropenia, monocytopenia, or lymphocytopenia, or subcombinations thereof) following whole body gamma irradiation in mice, with and without pretreatment with β-lapachone, is assessed as follows. β-lapachone is prepared at 10 mg/ml in 40% hydroxypropyl-beta-cyclodextrin (HPBCD). C57BL/6J inbred strain female mice (4-5 weeks old) are organized into three groups of six mice each: Group I mice receive no radiation, no β-lapachone, and no carrier; Group II mice receive radiation and are injected with carrier (40% HPBCD 4 ml/kg body weight); and Group III mice are injected intraperitoneally at 0.5 hour before irradiation with β-lapachone (40 mg/kg body weight). Whole body irradiation of animals with 8 Gy (lethal radiation) or 5 Gy (sublethal radiation) of γ-rays is carried out in air at room temperature in a gamma chamber (Gammacell 40 Exactor), with a dose-rate of 1.05 Gy/min. This radiation dose is within the range of equivalent human exposures predicted in many scenarios of radiologic or nuclear terrorist attack. Following irradiation, animals are maintained in a climate-controlled animal facility. Three mice in each of Groups I, II, and III are sacrificed on day five following irradiation, and an analysis of radiation-induced leukopenia is performed for each. The remaining mice are sacrificed on day eight following irradiation, and an analysis of radiation-induced leukopenia is performed for each. Leukocytes are counted automatically using a hemacytometer counter in the animal facility at MIT.

TABLE 7

| | Day 5 | | | | Day 8 | | | |
| --- | --- | --- | --- | --- | --- | --- | --- | --- |
| Treatment | WBC | N % | M % | L % | WBC | N % | M % | L % |
| Control | 2.72 ± 1.4 | 14.05 | 1.91 | 84.43 | 3.35 ± 0.13 | 14.92 | 3.69 | 79.7 |
| Radiation 8 Gy | 0.52 ± 0.4 | 26.93 | 7.97 | 47.61 | 0.2 ± 0.03 | 0 | 0 | 0 |
| β-lapachone → Radiation | 0.53 ± 0.4 | 19.1 | 8.13 | 66.24 | 0.37 ± 0.24 | 20.29 | 13.23 | 52.69 |

As shown in Table 7, gamma irradiated mice that were not pretreated with β-lapachone displayed profound leukopenia on days 5 and 8 after lethal radiation exposure (WBC expressed in 1000 cells/ml, with percentage of neutrophils, monocytes and lymphocytes.) Pretreatment with β-lapachone partially protects against this radiation-induced neutropenia, monocytopenia, and lymphocytopenia (For data corresponding to both day 5 and day 8, $P<0.05$). β-lapachone appears to have a moderate but substantial impact in preserving circulating leukocytes in the first eight days following exposure to lethal radiation (8 Gy).

Although the foregoing invention has been described in some detail by way of illustration and example for the purposes of clarity of understanding, one skilled in the art will easily ascertain that certain changes and modifications may be practiced without departing from the spirit and scope of the invention.

All references, patents and patent applications described herein are incorporated by reference in their entireties.

What is claimed:

1. A method of ameliorating or decreasing at least one symptom of radiation injury in a subject exposed to an accidental release of ionizing-radiation or an intentional release of ionizing-radiation from radiologic attack, wherein said subject does not have cancer or a cell-proliferative disorder, comprising administering to said subject, prior to said exposure, a therapeutically effective amount of β-lapachone or a pharmaceutically acceptable salt, in combination with a pharmaceutically acceptable carrier, wherein at least one said symptom of radiation injury is ameliorated or decreased.

2. The method of claim 1, wherein said radiation injury is caused by alpha radiation, beta radiation, gamma rays, or X-rays.

3. The method of claim 1, wherein said ameliorating or decreasing at least one symptom of radiation injury comprises decreasing cell death.

4. The method of claim 1, wherein said ameliorating or decreasing at least one symptom of radiation injury comprises decreasing cell death of immune cells.

5. The method of claim 1, wherein said ameliorating or decreasing at least one symptom of radiation injury comprises decreasing cell death of white blood cells.

6. The method of claim 1, wherein said ameliorating or decreasing at least one symptom of radiation injury comprises decreasing cell death of lymphocytes, monocytes, or neutrophils.

7. The method of claim 1, wherein said ameliorating or decreasing at least one symptom of radiation injury comprises ameliorating leukopenia.

8. The method of claim 1, wherein said ameliorating or decreasing at least one symptom of radiation injury comprises ameliorating neutropenia, monocytopenia, or lymphocytopenia.

9. The method of claim 1, wherein said ameliorating or decreasing at least one symptom of radiation injury comprises protecting the normal cellularity of the spleen or thymus.

10. A method of ameliorating or decreasing at least one symptom of radiation injury to normal cells in a subject exposed to an accidental release of ionizing-radiation or an intentional release of ionizing-radiation from radiologic attack, wherein said subject does not have cancer or a cell-proliferative disorder, comprising contacting a normal cell prior to said exposure, with an effective amount of β-lapachone, or a pharmaceutically acceptable salt, in combination with a pharmaceutically acceptable carrier, wherein at least one said symptom of radiation injury is ameliorated or decreased.

11. The method of claim 10, wherein said radiation injury is caused by alpha radiation, beta radiation, gamma rays, or X-rays.

12. The method of claim 10, wherein said normal cell is a normal immune cell.

13. The method of claim 10, wherein said normal cell is a normal white blood cell.

14. The method of claim 10, wherein said normal cell is a normal lymphocyte.

15. The method of claim 10, wherein said normal cell is a normal monocyte.

16. The method of claim 10, wherein said normal cell is a normal neutrophil.

17. The method of claim 10, wherein said ameliorating or decreasing at least one symptom of radiation injury comprises decreasing cell death.

18. A method of reducing radiation-induced neutropenia in a subject exposed to an accidental release of gamma-radiation or an intentional release of gamma-radiation from radiologic attack wherein said subject does not have cancer or a cell-proliferative disorder, comprising administering to said subject, prior to said exposure, a therapeutically effective amount of β-lapachone or a pharmaceutically acceptable salt, in combination with a pharmaceutically acceptable carrier.

19. A method of reducing radiation-induced monocytopenia in a subject exposed to an accidental release of gamma-radiation or an intentional release of gamma-radiation from radiologic attack wherein said subject does not have cancer or a cell-proliferative disorder, comprising administering to said subject, prior to said exposure, a therapeutically effective amount of β-lapachone or a pharmaceutically acceptable salt, in combination with a pharmaceutically acceptable carrier.

20. A method of reducing radiation-induced lymphocytopenia in a subject exposed to an accidental release of gamma-radiation or an intentional release of gamma-radiation from radiologic attack wherein said subject does not have cancer or a cell-proliferative disorder, comprising administering to said subject, prior to said exposure, a therapeutically effective amount of β-lapachone or a pharmaceutically acceptable salt, in combination with a pharmaceutically acceptable carrier.

* * * * *